United States Patent [19]
Meyer et al.

[11] Patent Number: 6,153,614
[45] Date of Patent: Nov. 28, 2000

[54] PIPERAZINYL PYRIMIDINE DIONE COMPOUNDS SELECTIVE FOR ADRENOCEPTORS

[75] Inventors: Michael D. Meyer, Lake Villa; William A. Carroll, Evanston, both of Ill.

[73] Assignee: Abbott Laboratories, Abbott Park, Ill.

[21] Appl. No.: 09/116,376

[22] Filed: Jul. 16, 1998

[51] Int. Cl.[7] .................. A61K 31/519; C07D 487/04; C07D 498/04; C07D 513/04
[52] U.S. Cl. .................. 514/252.16; 544/278; 544/280
[58] Field of Search .................. 544/278, 280; 514/253, 252.16

[56] References Cited

U.S. PATENT DOCUMENTS

| | | | |
|---|---|---|---|
| 4,670,560 | 6/1987 | Press et al. | 544/278 |
| 4,703,120 | 10/1987 | Press | 544/278 |
| 4,707,550 | 11/1987 | Press et al. | 544/379 |
| 4,835,157 | 5/1989 | Press et al. | 514/258 |
| 5,521,181 | 5/1996 | Meyer et al. | |

OTHER PUBLICATIONS

Romeo, G., et al., "Heterocyclic Systems Containing the Pyrimido–2,4–Dione Ring as Selective Ligands for the $\alpha_1$–Adrenoceptors", *IL Farmaco*, 50(6):471–477 (1995).

Russell, R. K., et al., "Thiophene Systems. 9. Thienopyrimidinedione Derivatives as Potential Antihypertensive Agents", *J. Med. Chem.*, 31:1786–1793 (1988).

*Primary Examiner*—Richard L. Raymond
*Attorney, Agent, or Firm*—Michael J. Ward

[57] ABSTRACT

Compounds of Formula I

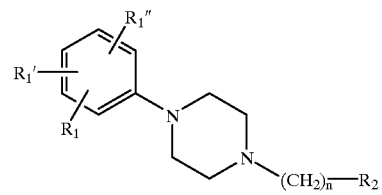

and II and their pharmaceutically acceptable, salts, esters and prodrugs thereof are selective alpha-1D adrenoceptor anatagonists and may be useful for treating disease states, such as benign prostatic hyperplasia, detrusor insatbility, and incontinence.

31 Claims, No Drawings

PIPERAZINYL PYRIMIDINE DIONE COMPOUNDS SELECTIVE FOR ADRENOCEPTORS

TECHNICAL FIELD

The present invention relates to compounds that are $a_1D$-adrenoceptor antagonists, pharmaceutical compositions containing these compounds, and methods of treatment using these compounds.

BACKGROUND OF THE INVENTION $\alpha_1$-Adrenergic receptors are widely distributed throughout both the central nervous system and the periphery where they mediate the effects of epinephrine and norepinephrine on the sympathetic nervous system. $\alpha_1$-Adrenoceptors play a central role in the maintenance of smooth muscle tone in both the prostate and the cardiovascular system (Ruffolo, R. R., Hieble, J. P. *Pharmac. Ther.* 1994, 61, 1–64). Antagonists of $\alpha_1$-adrenoceptors have shown beneficial effects both on ameliorating hypertension and alleviating the symptoms of benign prostatic hyperplasia (BPH) (Ruffolo, R. R., Bondinell, W., Hieble, J. P. *J. Med. Chem.* 1995,38, 3681–3716) by producing a smooth muscle relaxant effect in the target organs resulting from blockade of vascular or prostatic $\alpha_1$-receptors.

Recently, three distinct subtypes of the $\alpha_1$-adrenoceptor have been identified by both molecular biological ($\alpha_{1a}$, $\alpha_{1b}$, $\alpha_{1d}$) and classical pharmacological ($\alpha_{1A}$, $\alpha_{1B}$, $\alpha_{1D}$) means. The functional expression of the $\alpha_{1D}$-adrenoceptor subtype in various vascular beds has been demonstrated (Villalobos-Molina, R., Ibarra, M. *Eur. J. Pharmacol.* 1996, 298, 257–263; Piascik, M. T. et al. *J. Pharmacol. Exp. Ther.* 1995, 275, 1583–1589; Kenny, B. A. et al. *Br. J. Pharmacol.* 1995, 115, 981–986). Additionally, it has been shown that the $\alpha_{1D}$-adrenoceptor plays a significant role in maintaining blood pressure (Zhou, L., Vargas, H. M. *Eur. J. Pharmacol.* 1996, 305, 173–176; Deng, X. F., Chemtob, S., Varma, D. R. *Br. J. Pharmacol.* 1996, 119, 269–276) and that its role in maintaining blood pressure increases with the age of the mammal (Ibarra, M. et al. *Eur. J. Pharmacol.* 1997, 322, 221–224). Therefore, the utility of a selective $\alpha_{1D}$-antagonist in the treament of hypertension is indicated (Deng et al.). Also, approximately 30% of the mRNA in the prostate encodes for the $\alpha_{1D}$-adrenoceptor (Price, D. T. et al. *J. Urol.* 1993, 150, 546–541 which suggests a possible role in ameliorating the symptoms often associated with BPH. Additionally, it has been shown recently (Broten et al. *The FASEB Journal Abstracts Part* 1, (1998), 12 (4) A445) that the $\alpha_{1D}$-receptor is involved in mediating contractions associated with detrusor instability secondary to bladder outlet obstruction. It has also been shown recently that the $\alpha_{1D}$-receptor is the predominant $\alpha_1$ subtype present in the human bladder detrusor (Malloy, et al. in *J. of Urology,* (1998) 159, (5, Suppl.) 1263). The association of incontinence and the irritative symptoms of BPH with detrusor instability suggests that an $\alpha_{1D}$-antagonist capable of inhibiting detrusor contractions would be useful in the treatment of incontinence and BPH.

Russell and Press (U.S. Pat. No. 4,670,560 and *J. Med. Chem.* 1988, 31, 1786) describe thienopyrimidine-2,4-dione derivatives which are $\alpha_1$-antagonists and antihypertensive agents, and Meyer et al. (U.S. Pat. No. 5,521,181) describe phenyl substituted hexahydrobenz[e] isoindolylthienopyrimidine-2,4-diones which are $\alpha_1$-antagonists. However, these compounds are not selective for the $\alpha_{1D}$ subtype.

The present invention relates to novel $\alpha_{1D}$-adrenoceptor antagonist compounds, pharmaceutical compositions containing the compounds, and methods of treatment using these compounds.

SUMMARY OF THE INVENTION

The present invention relates to compounds that are $\alpha_{1D}$-adrenoceptor anatagonists, pharmaceutical compositions contining these compounds, and methods of treatment using these compounds.

The compounds of the present invention have the structure of Formula I

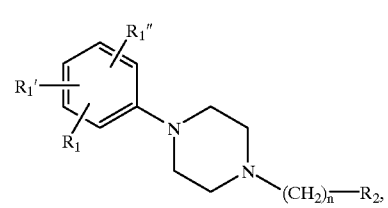

wherein $R_1$, $R_{1'}$, and $R_{1''}$ are independently selected from the group consisting of (a) halo, (b) hydroxy, (c) nitro, (d) amino, (e) N-protected amino, (f) haloalkoxy, (g) perfluoroalkoxy, (h) carboxy, (i) O-protected carboxy, (j) cycloalkoxy, (k) cycloalkyl, (l) cycloalkylalkyl, (m) alkoxy, (n) alkyl, (o) alkenyl, (p) alkenyloxy, (q) alkynyloxy, (r) alkynyl, (s) alkoxycarbonyl, and (t) hydrogen wherein ((j) –(s) can be optionally substituted with 1, 2, or 3 substituents independently selected from the group consisting of alkoxy, hydroxy, carboxy, O-protected carboxy, amino, N-protected amino, halo, hydroxy, and nitro;

n is 2–10; and $R_2$ is

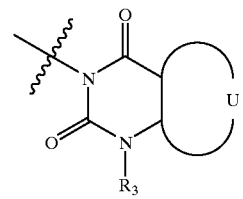

wherein U, taken together with the carbon atoms to which it is attached, forms a ring selected from the group consisting of (a) a mono- or disubstituted five-membered heterocycle having four carbon atoms, two double bonds, and one heteroatom selected from the group consisting of —N($R_5$)—, —O—, and —S— wherein $R_5$ is hydrogen, alkyl, alkenyl, alkynyl, cycloalkyl, cycloalkylalkyl, aryl, arylalkyl, heterocycle, and (heterocyclic)alkyl, and the mono- or di- substituents are independently selected from the group consisting of hydrogen, alkyl, alkenyl, alkynyl, cycloalkyl, cycloalkylalkyl, aryl, arylalkyl, heterocycle, and (heterocyclic)alkyl, with the proviso that at least one of $R_5$, mono-, or di- substituents is cycloalkyl, cycloalkylalkyl, aryl, arylalkyl, heterocyclic, or (heterocyclic)alkyl;

(b) a mono- or disubstituted five-membered heterocycle having three carbon atoms, two double bonds, and two heteroatoms selected from the group consisting of two nitrogen atoms, one oxygen atom and one nitrogen atom, and one sulphur atom and one nitrogen atom, and the mono- or di- substituents are independently selected from the group consisting of hydrogen, alkyl, alkenyl, alkynyl, cycloalkyl, cycloalkylalkyl, aryl, arylalkyl, heterocycle, and (heterocyclic)alkyl, with the proviso that at least one of the mono- or di- substituents is cycloalkyl, cycloalkylalkyl, aryl, arylalkyl, heterocyclic, or (heterocyclic)alkyl; and (c) a mono- or disubstituted six-membered heterocycle containing three double bonds and either one, two, or three nitogen atoms, and the mono- or di- substituents are independently selected from the group consisting of hydrogen, alkyl, alkenyl, alkynyl, cycloalkyl, cycloalkylalkyl, aryl, arylalkyl, heterocycle, and (heterocyclic)alkyl, with the proviso that at least one of the mono- or di- substituents is cycloalkyl, cycloalkylalkyl, aryl, arylalkyl, heterocyclic, or (heterocyclic)alkyl; and wherein $R_3$ is selected from the group consisting of hydrogen, alkyl, alkenyl, alkynyl, cycloalkyl, and cycloalkylalkyl.

DETAILED DESCRIPTION OF THE INVENTION

The compounds of the present invention have the structure of Formula I

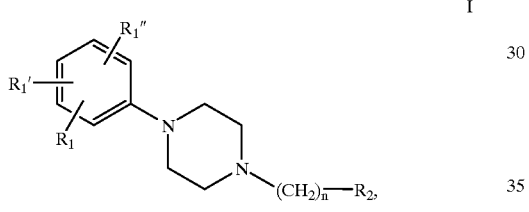

I wherein $R_1$, $R_{1'}$, and $R_{1''}$ are independently selected from the group consisting of (a) halo, (b) hydroxy, (c) nitro, (d) amino, (e) N-protected amino, (f) haloalkoxy, (g) perfluoroalkoxy, (h) carboxy, (i) O-protected carboxy, (j) cycloalkoxy, (k) cycloalkyl, (l) cycloalkylalkyl, (m) alkoxy, (n) alkyl, (o) alkenyl, (p) alkenyloxy, (q) alkynyloxy, (r) alkynyl, (s) alkoxycarbonyl, and (t) hydrogen wherein (j)–(s) can be optionally substituted with 1, 2, or 3 substituents independently selected from the group consisting of alkoxy, hydroxy, carboxy, O-protected carboxy, amino, N-protected amino, halo, hydroxy, and nitro;

n is 2–10; and $R_2$ is

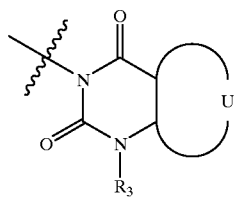

wherein U, taken together with the carbon atoms to which it is attached, forms a ring selected from the group consisting of (a) a mono- or disubstituted five-membered heterocycle having four carbon atoms, two double bonds, and one heteroatom selected from the group consisting of —N($R_5$)—, —O—, and —S— wherein $R_5$ is hydrogen, alkyl, alkenyl, alkynyl, cycloalkyl, cycloalkylalkyl, aryl, arylalkyl, heterocycle, and (heterocyclic)alkyl, and the mono- or di- substituents are independently selected from the group consisting of hydrogen, alkyl, alkenyl, alkynyl, cycloalkyl, cycloalkylalkyl, aryl, arylalkyl, heterocycle, and (heterocyclic)alkyl, with the proviso that at least one of $R_5$, mono-, or di- substituents is cycloalkyl, cycloalkylalkyl, aryl, arylalkyl, heterocyclic, or (heterocyclic)alkyl;

(b) a mono- or disubstituted five-membered heterocycle having three carbon atoms, two double bonds, and two heteroatoms selected from the group consisting of two nitrogen atoms, one oxygen atom and one nitrogen atom, and one sulphur atom and one nitrogen atom, and the mono- or di- substituents are independently selected from the group consisting of hydrogen, alkyl, alkenyl, alkynyl, cycloalkyl, cycloalkylalkyl, aryl, arylalkyl, heterocycle, and (heterocyclic)alkyl, with the proviso that at least one of the mono- or di- substituents is cycloalkyl, cycloalkylalkyl, aryl, arylalkyl, heterocyclic, or (heterocyclic)alkyl; and (c) a mono- or disubstituted six-membered heterocycle containing three double bonds and either one, two, or three nitogen atoms, and the mono- or di- substituents are independently selected from the group consisting of hydrogen, alkyl, alkenyl, alkynyl, cycloalkyl, cycloalkylalkyl, aryl, arylalkyl, heterocycle, and (heterocyclic)alkyl, with the proviso that at least one of the mono- or di- substituents is cycloalkyl, cycloalkylalkyl, aryl, arylalkyl, heterocyclic, or (heterocyclic)alkyl; and wherein $R_3$ is selected from the group consisting of hydrogen, alkyl, alkenyl, alkynyl, cycloalkyl, and cycloalkylalkyl.

Another embodiment of the the present invention includes a compound of Formula I wherein U is

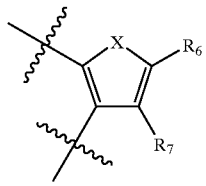

wherein X is selected from the group consisting of —N($R_5$)—, —O—, and —S— wherein $R_5$, $R_6$ and $R_7$ are independently selected from the group consisting of hydrogen, alkyl, alkenyl, alkynyl, cycloalkyl, cycloalkylalkyl, aryl, arylalkyl, heterocycle, and (heterocyclic)alkyl, with the proviso that at least one of $R_5$, $R_6$ and $R_7$ cycloalkyl, cycloalkylalkyl, aryl, arylalkyl, heterocyclic, or (heterocyclic)alkyl; or a pharmaceutically accceptable salt, ester, or prodrug thereof.

Another embodiment of the present invention includes a compound of Formula I wherein U is

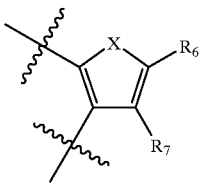

wherein X is selected from the group consisting of —N(R$_5$)—, —O—, and —S—, n is 2–5, R$_3$ is hydrogen or alkyl, R$_1$, R$_{1'}$ and R$_{1''}$ are independently selected from hydrogen and alkoxy, and R$_5$, R$_6$ and R$_7$ are independently hydrogen or aryl with the proviso that at least one of R$_5$, R$_6$ and R$_7$ is aryl; or a pharmaceutically acceptable salt, ester or prodrug thereof.

Another embodiment of the present invention includes a compound or a pharmaceutically acceptable salt, ester or prodrug of Formula I, wherein U is

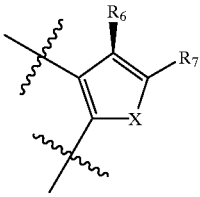

wherein X is selected from the group consisting of —N(R$_5$)—, —O—, and —S— wherein R$_5$, R$_6$ and R$_7$ are independently selected from the group consisting of hydrogen, alkyl, alkenyl, alkynyl, cycloalkyl, cycloalkylalkyl, aryl, arylalkyl, heterocycle, and (heterocyclic)alkyl, with the proviso that at least one of R$_5$, R$_6$ and R$_7$ is cycloalkyl, cycloalkylalkyl, aryl, arylalkyl, heterocyclic, or (heterocyclic)alkyl.

Another embodiment of the present invention includes a compound of Formula I wherein U is

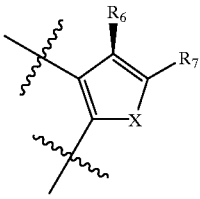

X is selected from the group consisting of —N(R$_5$)—, —O—, and —S—, n is 2–5, R$_3$ is hydrogen or alkyl, R$_1$, R$_{1'}$, and R$_{1''}$ are independently selected from hydrogen and alkoxy, and R$_5$, R$_6$ and R$_7$ are independently hydrogen or aryl with the proviso that at least one of R$_5$, R$_6$ and R$_7$ is aryl; or a pharmaceutically acceptable salt, ester or prodrug thereof.

Another embodiment of the present invention includes a compound or a pharmaceutically acceptable salt, ester or prodrug of Formula I wherein U is

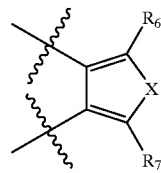

wherein X is selected from the group consisting of —N(R$_5$)—, —O—, and —S— wherein R$_5$, R$_6$ and R$_7$ are independently selected from the group consisting of hydrogen, alkyl, alkenyl, alkynyl, cycloalkyl, cycloalkylalkyl, aryl, arylalkyl, heterocycle, and (heterocyclic)alkyl, with the proviso that at least one of R$_5$, R$_6$ and R$_7$ cycloalkyl, cycloalkylalkyl, aryl, arylalkyl, heterocyclic, or (heterocyclic)alkyl.

Another embodiment of the present invention includes a compound or a pharmaceutically acceptable salt, ester or prodrug of Formula I wherein U is

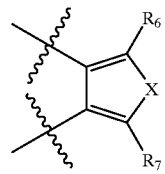

wherein X is selected from the group consisting of —N(R$_5$)—, —O—, and —S—, n is 2–5, R$_3$ is hydrogen or alkyl, R$_1$, R$_{1'}$, and R$_{1''}$ are independently selected from hydrogen and alkoxy, and R$_5$, R$_6$ and R$_7$ are independently hydrogen or aryl, with the proviso that at least one of R$_5$, R$_6$ and R$_7$ is aryl.

Another embodiment of the present invention includes a compound of Formula I or a pharmaceutically acceptable salt, ester or prodrug thereof wherein n is 2–5, U is a mono- or disubstituted five-membered heterocycle having three carbon atoms, two double bonds, and two heteroatoms selected from the group consisting of two nitrogen atoms, one oxygen atom and one nitrogen atom, and one sulphur atom and one nitrogen atom, and the mono- or di- substituents are independently selected from the group consisting of hydrogen, alkyl, alkenyl, alkynyl, cycloalkyl, cycloalkylalkyl, aryl, arylalkyl, heterocycle, and (heterocyclic)alkyl, with the proviso that at least one of the mono- or di- substituents is cycloalkyl, cycloalkylalkyl, aryl, arylalkyl, heterocyclic, or (heterocyclic)alkyl; and R$_1$, R$_{1'}$, and R$_{1''}$ are independently selected from (a) halo, (b) hydroxy, (c) nitro, (d) amino, (e) N-protected amino, (f) haloalkoxy, (g) perfluoroalkoxy, (h) carboxy, (i) O-protected carboxy, (j) cycloalkoxy, (k) cycloalkyl, (l) cycloalkylalkyl, (m) alkoxy, (n) alkyl, (o) alkenyl, (p) alkenyloxy, (q) alkynyloxy, (r) alkynyl, and (s) alkoxycarbonyl wherein (j)–(s) can be optionally substituted with 1, 2, or 3 substituents independently selected from the group consisting of alkoxy, hydroxy, carboxy, O-protected carboxy, amino, N-protected amino, halo, hydroxy, and nitro.

Another embodiment of the present invention includes a compound of Formula I or a pharmaceutically acceptable salt, ester or prodrug wherein n is 2–5, U is a mono- or disubstituted six-membered heterocycle containing three double bonds and either one, two, or three nitogen atoms, and the mono- or di- substituents are independently selected from the group consisting of hydrogen, alkyl, alkenyl, alkynyl, cycloalkyl, cycloalkylalkyl, aryl, arylalkyl, heterocycle, and (heterocyclic)alkyl, with the proviso that at least one of the mono- or di- substituents is cycloalkyl, cycloalkylalkyl, aryl, arylalkyl, heterocyclic, or (heterocyclic)alkyl; and and $R_1$, $R_{1'}$, and $R_{1''}$ are independently selected from the group consisting of (a) halo, (b) hydroxy, (c) nitro, (d) amino, (e) N-protected amino, (f) haloalkoxy, (g) perfluoroalkoxy, (h) carboxy, (i) O-protected carboxy, (j) cycloalkoxy, (k) cycloalkyl, (l) cycloalkylalkyl, (m) alkoxy, (n) alkyl, (o) alkenyl, (p) alkenyloxy, (q) alkynyloxy, (r) alkynyl, and (s) alkoxycarbonyl wherein (j)–(s) can be optionally substituted with 1, 2, or 3 substituents independently selected from the group consisting of alkoxy, hydroxy, carboxy, O-protected carboxy, amino, N-protected amino, halo, hydroxy, and nitro.

Yet another embodiment of the present invention includes a compound of Formula II

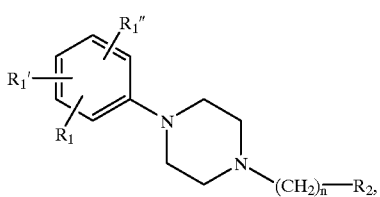

II or a pharmaceutically acceptable salt, ester or prodrug thereof, wherein $R_1$, $R_{1'}$, and $R_{1''}$ are independently selected from the group consisting of (a) halo, (b) hydroxy, (c) nitro, (d) amino, (e) N-protected amino, (f) haloalkoxy, (g) perfluoroalkoxy, (h) carboxy, (i) O-protected carboxy, (j) cycloalkoxy, (k) cycloalkyl, (l) cycloalkylalkyl, (m) alkoxy, (n) alkyl, (o) alkenyl, (p) alkenyloxy, (q) alkynyloxy, (r) alkynyl, (s) alkoxycarbonyl, and (t) hydrogen wherein (j)–(s) can be optionally substituted with 1, 2, or 3 substituents independently selected from the group consisting of alkoxy, hydroxy, carboxy, O-protected carboxy, amino, N-protected amino, halo, hydroxy, and nitro;

n is 2–5; and $R_2$ is selected from the group consisting of

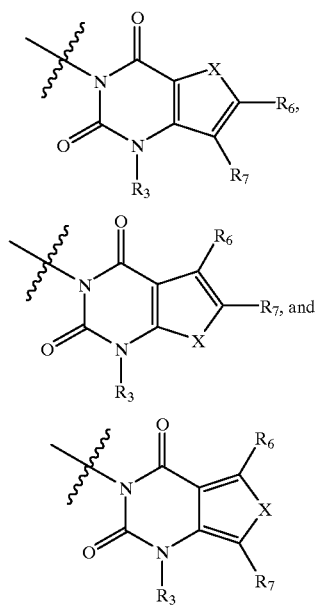

wherein at each occurence X is selected from the group consisting of —N($R_5$)—, —O—, and —S— wherein $R_5$, $R_6$ and $R_7$ are independently selected from the group consisting of hydrogen, alkyl, alkenyl, alkynyl, cycloalkyl, cycloalkylalkyl, aryl, arylalkyl, heterocycle, and (heterocyclic)alkyl, with the proviso that at least one of $R_5$, $R_6$ and $R_7$ is cycloalkyl, cycloalkylalkyl, aryl, arylalkyl, heterocyclic, or (heterocyclic)alkyl, and $R_3$ is selected from the group consisting of hydrogen, alkyl, alkenyl, alkynyl, cycloalkyl, and cycloalkylalkyl.

Yet another embodiment of the present invention includes a compound or a pharmaceutically acceptable salt, ester or prodrug thereof of Formula II wherein $R_2$ is

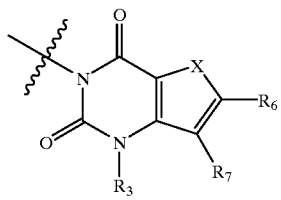

wherein X is selected from the group consisting of —N($R_5$)—, —O—, and —S— wherein $R_5$, $R_6$ and $R_7$ are independently selected from the group consisting of hydrogen and aryl with the proviso that at least one of $R_5$, $R_6$ and $R_7$ is aryl, and $R_3$ is selected from the group consisting of hydrogen and alkyl.

Yet another embodiment of the present invention includes a compound of Formula II or a pharmaceutically acceptable salt, ester or prodrug wherein $R_2$ is

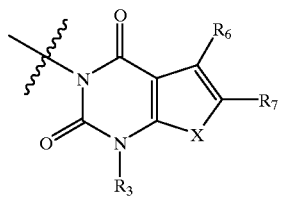

wherein X is selected from the group consisting of —N($R_5$)—, —O—, and —S— wherein $R_5$, $R_6$ and $R_7$ are independently selected from the group consisting of hydrogen and aryl with the proviso that at least one of $R_5$, $R_6$ and $R_7$ is aryl, and $R_3$ is selected from the group consisting of hydrogen and alkyl.

Yet another embodiment of the present invention includes a compound of Formula II or a pharmaceutically acceptable salt, ester or prodrug wherein $R_2$ is

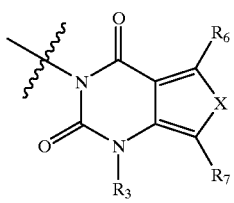

wherein X is selected from the group consisting of —N($R_5$)—, —O—, and —S— wherein $R_5$, $R_6$ and $R_7$ are independently selected from the group consisting of hydrogen and aryl with the proviso that at least one of $R_5$, $R_6$ and $R_7$ is aryl, and $R_3$ is selected from the group consisting of hydrogen and alkyl.

Yet another embodiment of the present invention includes a compound of Formula H or a pharmaceutically acceptable salt, ester or prodrug thereof wherein $R_2$ is

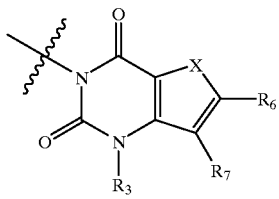

wherein $R_1$, $R_{1'}$, and $R_{1''}$ are independently selected from the group consisting of hydrogen and alkoxy, n is 2, X is selected from the group consisting of —N($R_5$)— and —S— wherein $R_5$, $R_6$ and $R_7$ are independently selected from the group consisting of hydrogen and aryl with the proviso that at least one of $R_5$, $R_6$ and $R_7$ is aryl, and $R_3$ is hydrogen or alkyl Yet another embodiment of the present invention includes a compound or a pharmaceutically acceptable salt, ester or prodrug wherein $R_2$ is

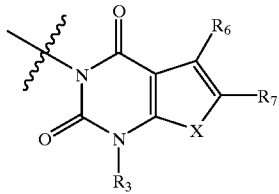

wherein $R_1$, $R_{1'}$, and $R_{1''}$ are independently selected from the group consisting of hydrogen and alkoxy, n is 2, X is selected from the group consisting of —N($R_5$)— and —S— wherein $R_5$, $R_6$ and $R_7$ are independently selected from the group consisting of hydrogen and aryl with the proviso that at least one of $R_5$, $R_6$ and $R_7$ is aryl, and $R_3$ is hydrogen or alkyl.

Yet another embodiement of the present invention includes a compound of Formula II or a pharmaceutically acceptable salt, ester or prodrug thereof wherein $R_2$ is

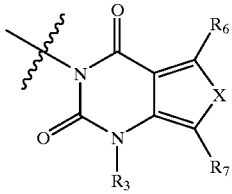

wherein $R_1$, $R_{1'}$, and $R_{1''}$ are independently selected from the group consisting of hydrogen and alkoxy, n is 2, X is selected from the group consisting of —N($R_5$)— and —S— wherein $R_5$, $R_6$ and $R_7$ are independently selected from the group consisting of hydrogen and aryl with the proviso that at least one of $R_5$, $R_6$ and $R_7$ is aryl and $R_3$ is hydrogen or alkyl.

In another embodiment of the invention is disclosed a method of antagonizing $\alpha_{1D}$-adrenoceptors in a host mammal, particularly humans, in need of such treatment by administering a therapeutically effective amount of a compound of Formula I or II.

In yet another embodiment of the invention is disclosed a method of treating benign prostatic hyperplasia, hypertension, detrusor instability, and incontinence in a mammal, particularly humans, in need of such treatment by administering an effective amount of a compound of Formula I or II.

In still yet another embodiment of the invention is disclosed pharmaceutical compositions which comprise a therapeutically effective amount of a compound of Formula I or II in combination with a pharmaceutically effective carrier.

DEFINITION OF TERMS

The term "alkenyl" refers to a monovalent straight or branched chain group of 2–10 carbons derived from a hydrocarbon having at least one carbon-carbon double bond.

The term "alkenyloxy" as used herein refers to an alkenyl group of 3–10 carbons attached to the parent molecular group through an oxygen atom.

The term "alkoxy" as used herein refers to an alkyl group as defined herein attatched to the parent molecular group through an oxygen atom. Examples of alkoxy include, but are not limited to, methoxy, ethoxy, t-butoxy, and the like.

The term "alkoxycarbonyl" refers to an ester group, i.e. an alkoxy group attached to the parent molecular group through a carbonyl group.

The term "alkyl" or "loweralkyl" as used herein refers to a straight or branched chain alkyl radical containing from 1 to 10 carbon atoms including, but not limited to, methyl, ethyl, n-propyl, iso-propyl, n-butyl, iso-butyl, sec-butyl, t-butyl, n-pentyl, 1-methylbutyl, 2,2-dimethylbutyl, 2-methylpentyl, 2,2-dimethylpropyl, 2-methylpentyl, 2,2-dimethylpropyl, n-hexyl, and the like.

The term "alkylamino" as used herein refers to an amino group wherein one of the hydrogens has been replaced with an alkyl group.

The term "alkynyl" as used herein refers to a monovalent straight or branched chain hydrocarbon of 2–10 carbons with at least one carbon-carbon triple bond.

The term "alkynyloxy" as used herein refers to an alkynyl group of 3–10 carbons attached to the parent molecular group through an oxygen atom.

The term "amino" as used herein refers to —$NH_2$.

The term "aryl" as used herein refers to a mono- or bicyclic carbocyclic ring system having one or more aromatic rings including, but not limited to, phenyl, naphthyl, tetrahydronaphthyl, naphthyridinyl, indanyl, indenyl and the like. Aryl groups can be unsubstituted or substituted with one, two or three substituents independently selected from the group consisting of loweralkyl, haloalkyl, alkoxy, thioalkoxy, amino, alkylamino, dialkylamino, hydroxy, halo, mercapto, nitro, carboxaldehyde, carboxy, alkoxycarbonyl and carboxamide. In addition, substituted aryl groups include tetrafluorophenyl and pentafluorophenyl.

The term "arylalkyl" as used herein refers to an aryl group as previously defined, appended to a loweralkyl radical. Examples of arylalkyl are benzyl, phenethyl, and the like.

The term "carboxy" as used herein refers to —$CO_2H$.

The term "carboxaldehyde" as used herein refers to —CHO.

The term "carboxamide" as used herein refers to an amino, alkylamino, or dialkylamino group attached to the parent molecular group through a carbonyl group.

The term "cycloalkoxy" as used herein refers to an cycloalkyl group as defined herein attached to the parent molecular group through an oxygen atom. Cycloalkoxy groups can be unsubstituted or substituted with one, two or three substituents independently selected from loweralkyl, haloalkyl, alkoxy, thioalkoxy, amino, alkylamino, dialkylamino, hydroxy, halo, mercapto, nitro, carboxaldehyde, carboxy, alkoxycarbonyl and carboxamide.

The term "cycloalkyl" as used herein refers to an aliphatic ring system having 3 to 10 carbon atoms and 1 to 3 rings including, but not limited to, cyclopropyl, cyclopentyl, cyclohexyl, norbornyl, adamantyl, and the like. Cycloalkyl groups can be unsubstituted or substituted with one, two or three substituents independently selected from loweralkyl, haloalkyl, alkoxy, thioalkoxy, amino, alkylamino, dialkylamino, hydroxy, halo, mercapto, nitro, carboxaldehyde, carboxy, alkoxycarbonyl and carboxamide.

The term "cycloalkylalkyl" as used herein refers to a cycloalkyl group as defined herein appended to a loweralkyl radical. Cycloalkylalkyl groups include but are not limited to cyclopropylmethyl, cyclohexylethyl, and the like. Cycloalkylalkyl groups can be unsubstituted or substituted with one, two or three substituents independently selected from loweralkyl, haloalkyl, alkoxy, thioalkoxy, amino, alkylamino, dialkylamino, hydroxy, halo, mercapto, nitro, carboxaldehyde, carboxy, alkoxycarbonyl and carboxamide.

The term "dialkylamino" as used herein refers to an amino group wherein each of the hydrogens has been replaced with an alkyl group.

The term "halo" as used herein refers to F, Cl, Br and I.

The term "haloalkoxy" as used herein refers to a haloalkyl group as defined herein attached to the parent molecular group through an oxygen atom.

The term "haloalkyl" as used herein refers to an alkyl group as defined herein to which is attached one or more halo substituents.

The terms "heterocyclic ring" or "heterocyclic" or "heterocycle" as used herein refers to any 3- or 4-membered ring containing a heteroatom selected from oxygen, nitrogen and sulfur; or a 5-, 6- or 7-membered ring containing one, two or three nitrogen atoms; one nitrogen and one sulfur atom; or one nitrogen and one oxygen atom, or one sulphur atom, or one oxygen atom. The 5-membered ring has 0–2 double bonds and the 6- and 7-membered ring have 0–3 double bonds. The nitrogen heteroatoms can be optionally quaternized. The term "heterocyclic" also includes bicyclic groups in which any of the above heterocyclic rings is fused to a benzene ring or a cyclohexane ring or another heterocyclic ring (for example, indolyl, quinolyl, isoquinolyl, tetrahydroquinolyl, benzofuryl or benzothienyl and the like). Heterocyclics include: azetidinyl, pyrrolyl, pyrrolinyl, pyrrolidinyl, pyrazolyl, pyrazolinyl, pyrazolidinyl, imidazolyl, imidazolinyl, imidazolidinyl, pyridyl, piperidinyl, homopiperidinyl, pyrazinyl, piperazinyl, pyrimidinyl, pyridazinyl, oxazolyl, oxazolidinyl, isoxazolyl, isoxazolidinyl, morpholinyl, thiazolyl, thiazolidinyl, isothiazolyl, isothiazolidinyl, indolyl, quinolinyl, isoquinolinyl, benzimidazolyl, benzothiazolyl, benzoxazolyl, furyl, thienyl and benzothienyl.

Heterocyclics can be unsubstituted or monosubstituted or disubstituted with substituents independently selected from hydroxy, halo, oxo (=O), alkylimino (R*N=wherein R* is a loweralkyl group), amino, alkylamino, dialkylamino, alkoxy, alkoxyalkoxy, haloalkyl, cycloalkyl, aryl, arylalkyl, —COOH, —SO₃H, nitro, and loweralkyl. In addition, nitrogen containing heterocycles can be N-protected.

The term "(heterocyclic)alkyl" as used herein refers to a heterocyclic group as defined above appended to a loweralkyl radical as defined above.

The term "hydroxy" as used herein refers to —OH.

The term "mercapto as used herein, refers to —SH.

The term "N-protected amino" or "N-protected nitrogen" as used herein refers to an amino group to which is attached an N-protecting or nitrogen-protecting group. The term "nitrogen protecting group" as used herein, refers to those groups intended to protect an amino group against undersirable reactions during synthetic procedures. N-protecting groups comprise acyl groups such as formyl, acetyl, propionyl, pivaloyl, t-butylacetyl, 2-chloroacetyl, 2-bromoacetyl, trifluoroacetyl, trichloroacetyl, phthalyl, o-nitrophenoxyacetyl, α-chlorobutyryl, benzoyl, 4-chlorobenzoyl, 4-bromobenzoyl, 4-nitrobenzoyl and chiral auxiliaries such as protected or unprotected D, L or D, L-amino acids such as alanine, leucine, phenylalanine, and the like; sulfonyl groups such as benzenesulfonyl, p-toluenesulfonyl and the like; carbamate forming groups such as benzyloxycarbonyl, p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxycarbonyl, t-butyloxycarbonyl, diisopropylmethoxycarbonyl, isopropyloxycarbonyl, ethoxycarbonyl, methoxycarbonyl, allyloxycarbonyl, 2,2,2,-trichloroethoxycarbonyl, phenoxycarbonyl, 4-nitrophenoxy carbonyl, fluorenyl-9-methoxycarbonyl, cyclopentyloxycarbonyl, adamantyloxycarbonyl, cyclohexyloxycarbonyl, phenylthiocarbonyl and the like; arylalkyl groups such as benzyl, triphenylmethyl, benzyloxymethyl and the like and silyl groups such as trimethylsilyl and the like. Preferred N-protecting groups are formyl, acetyl, benzoyl, pivaloyl, t-butylacetyl, phenylsulfonyl, benzyl, t-butyloxycarbonyl (Boc) and benzyloxycarbonyl (Cbz).

The term "nitro" as used herein refers to —NO₂.

The term "O-protected carboxy" as used herein refers to an ester or amide group intended to protect a carboxy group against undersirable reactions during synthetic procedures. Additionally, a carboxy protecting group can be used as a prodrug whereby the carboxy protecting group can be readily cleaved in vivo, for example, by enzymatic hydrolysis, to release the biologically-active parent compound. Such carboxy protecting groups are well-known to those skilled in the art, having been extensively used in the protection of carboxyl groups in the penicillin and cephalosporin fields as described in U.S. Pat. Nos. 3,840,556 and 3,719,667, the disclosures of which are incorporated herein by reference. Representative carboxy protecting groups are $C_1$–$C_8$ loweralkyl (e.g., methyl, ethyl or t-butyl and the like); arylalkyl such as phenethyl or benzyl and substituted derivatives thereof such as alkoxybenzyl or nitrobenzyl groups and the like; arylalkenyl such as phenylethenyl and the like; aryl and substituted derivatives thereofsuch as 5-indanyl and the like; dialkylaminoalkyl such as dimethylaminoethyl and the like); alkanoyloxyalkyl groups such as acetoxymethyl, butyryloxymethyl, valeryloxymethyl, isobutyryloxymethyl, isovaleryloxymethyl, 1-(propionyloxy)-1-ethyl, 1-(pivaloyloxyl)-1-ethyl, 1-methyl-1-(propionyloxy)-1-ethyl, pivaloyloxymethyl, propionyloxymethyl and the like; cycloalkanoyloxyalkyl groups such as cyclopropylcarbonyloxymethyl, cyclobutylcarbonyloxymethyl, cyclopentylcarbonyloxymethyl, cyclohexylcarbonyloxymethyl and the like; aroyloxyalkyl such as benzoyloxymethyl, benzoyloxyethyl and the like; arylalkylcarbonyloxyalkyl such as benzylcarbonyloxymethyl, 2-benzylcarbonyloxyethyl and the like; alkoxycarbonylalkyl or cycloalkyloxycarbonylalkyl such as methoxycarbonylmethyl, cyclohexyloxycarbonylmethyl, 1-methoxycarbonyl-1-ethyl and the like; alkoxycarbonyloxyalkyl or cycloalkyloxycarbonyloxyalkyl such as methoxycarbonyloxymethyl, t-butyloxycarbonyloxymethyl, 1-ethoxycarbonyloxy-1-ethyl, 1-cyclohexyloxycarbonyloxy-1-ethyl and the like; aryloxycarbonyloxyalkyl such as 2-(phenoxycarbonyloxy)ethyl, 2-(5-indanyloxycarbonyloxy)ethyl and the like; alkoxyalkylcarbonyloxyalkyl such as 2-(1-methoxy-2-methylpropan-2-oyloxy)ethyl and like; arylalkyloxycarbonyloxyalkyl such as 2-(benzyloxycarbonyloxy)ethyl and the like; arylalkenyloxycarbonyloxyalkyl such as 2-(3-phenylpropen-2-yloxycarbonyloxy)ethyl and the like; alkoxycarbonylaminoalkyl such as t-butyloxycarbonylaminomethyl and the like; alkylaminocarbonylaminoalkyl such as methylaminocarbonylaminomethyl and the like; alkanoylaminoalkyl such as acetylaminomethyl and the like; heterocycliccarbonyloxyalkyl such as 4-methylpiperazinylcarbonyloxymethyl and the like; dialkylaminocarbonylalkyl such as dimethylaminocarbonylmethyl, diethylaminocarbonylmethyl and the like; (5-(loweralkyl)-2-oxo-1,3-dioxolen-4-yl)alkyl such as (5-t-butyl-2-oxo-1,3-dioxolen-4-yl)methyl and the like; and (5-phenyl-2-oxo-1,3-dioxolen-4-yl)alkyl such as (5-phenyl-2-oxo-1,3-dioxolen-4-yl)methyl and the like.

The term "perfluoroalkoxy" as used herein refers to a perfluoroalkyl group as defined herein attached to the parent molecular group through an oxygen atom.

The term "perfluoroalkyl" as used herein refers to an alkyl group as defined herein in which all of the hydrogen radicals have been substituted with fluoride radicals.

The term "pharmaceutically acceptable prodrug" as used herein refers to those prodrugs of the compounds of the present invention which are, within the scope of sound medical judgement, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the invention.

The term "pharmaceutically acceptable salt" as use herein refers to those salts which are, within the scope of sound medical judgement, suitable for use in contact with the tissues of humans and lower animals without undue toxicity, irritation, allergic response and the like and are commensurate with a reasonable benefit/risk ratio. Pharmaceutically acceptable salts are well-known in the art. For example, S. M Berge, et al. describe pharmaceutically acceptable salts in detail in J. Pharmaceutical Sciences, 1977, 66:1–19. The salts can be prepared in situ during the final isolation and purification of the compounds of the invention or separately by reacting the free base group with a suitable organic acid. Representative acid addition salts include acetate, adipate, alginate, ascorbate, aspartate, benzenesulfonate, benzoate, bisulfate, borate, butyrate, camphorate, camphersulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxyethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts and the like. Representative alkali or alkaline earth metal salts include sodium, lithium, potassium, calcium, magnesium and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine and the like.

The term "prodrug" as used herein refers to compounds which are rapidly transformed in vivo to the parent compound of Formula I and II, for example, by hydrolysis in blood. A thorough discussion is provided in T. Higuchi and V. Stella, Prodrugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987, both of which are incorporated herein by reference.

The term "thioalkoxy" as used herein refers to an alkoxy group as defined herein attatched to the parent molecular group through a sulfur atom. Examples of alkoxy include, but are not limited to, thiomethoxy, thioethoxy, and the like.

It is contemplated to be within the scope of the present invention that prodrugs may be used and subsequently converted in vivo into the compounds of the present invention.

Asymmetric or chiral centers may exist in the compounds of the present invention. The present invention contemplates the various stereoisomers and mixtures thereof. Individual stereoisomers of compounds of the present invention are prepared synthetically from commercially available starting materials which contain asymmetric or chiral centers or by preparation of mixtures of enantiomeric compounds followed by resolution well-known to those of ordinary skill in the art. These methods of resolution are exemplified by (1) attachment of a racemic mixture of enantiomers, designated (±), to a chiral auxiliary, separation of the resulting diastereomers by recrystallization or chromatography and liberation of the optically pure product from the auxiliary or (2) direct separation of the mixture of optical enantiomers on chiral chromatographic columns. Enantiomers are designated herein by the symbols "R" or "S," depending on the configuration of subsitiuents around the chiral carbon atom.

Geometric isomers may also exist in the compounds of the present invention. The present invention contemplates the various geometric isomers and mixtures thereof resulting from the arrangement of substituents around a carbon-carbon double bond and designates such isomers as of the Z or E configuration, wherein the term "Z" represents substituents on the same side of the carbon-carbon double bond and the term "E" represents substituents on opposite sides of the carbon-carbon double bond.

Compounds falling within the scope of Formula I and II include, but are not limited to, 3-[4-(2-methoxyphenyl)piperazinylethyl]-5-phenylthieno[2,3-d]pyrimidine-2,4-dione, 3-[4-(2-methoxyphenyl)piperazinylethyl]-6-methyl-5-phenylthieno[2,3-d]pyrimidine-2,4-dione, 3-[4-(2-methoxyphenyl)piperazinylethyl]-1-methyl-5-phenylthieno[2,3-d]pyrimidine-2,4-dione, 3-[4-(2-methoxyphenyl)piperazinylethyl]-5-(3-methylphenyl)thieno[2,3-d]pyrimidine-2,4-dione, and 3-[4-(2-methoxyphenyl)piperazinylethyl]-6-phenylthieno[2,3-d]pyrimidine-2,4-dione, 3-[2-[4-(2-methoxyphenyl)-1-piperazinyl]ethyl]-5-phenylfuro[2,3-d]pyrimidine-2,4(1H,3H)-dione,
3-[2-[4-(2-methoxyphenyl)-1-piperazinyl]ethyl]-5-phenyl-1H-pyrrolo[2,3-d]pyrimidine-2,4(3H,7H)-dione,
3-[2-[4-(2-methoxyphenyl)-1-piperazinyl]ethyl]-5-phenylfuro[2,3-d]pyrimidine-2,4(1H,3H)-dione,
3-[2-[4-(2-methoxyphenyl)-1-piperazinyl]ethyl]-6-phenyl-1H-pyrrolo[2,3-d]pyrimidine-2,4(3H,7H)-dione,
3-[2-[4-(2-methoxyphenyl)-1-piperazinyl]ethyl]-7-phenyl[3,4-d]pyrimidine-2,4(1H,6H)-dione,
3-[2-[4-(2-methoxyphenyl)-1-piperazinyl]ethyl]-7-phenylthieno[3,4-d]pyrimidine-2,4(1H,3H)-3-[2-[4-(2-methoxyphenyl)-1-piperazinyl]ethyl]-5-phenylthieno[3,4d]pyrimidine-2,4(1H,3H)-3-[2-[4-(2-methoxyphenyl)-1-piperazinyl]ethyl]-7-phenylfuro[3,2-d]pyrimidine-2,4(1H,3H)-dione,
3-[2-[4-(2-methoxyphenyl)-1-piperazinyl]ethyl]-6-phenylthieno[3,2-d]pyrimidine-2,4(1H,3H)-3-[2-[4-(2-methoxyphenyl)-1-piperazinyl]ethyl]-7-phenylthieno[3,2-d]pyrimidine-2,4(1H,3H)-dione; or a pharmaceutically acceptable salt, ester or prodrug thereof Preferred Compounds falling within the scope of Formula I and II include, but are not limited to,
3-[4-(2-methoxyphenyl)piperazinylethyl]-5-phenylthieno[2,3-d]pyrimidine-2,4-dione,
3-[4-(2-methoxyphenyl)piperazinylethyl]-6-methyl-5-phenylthieno[2,3-d]pyrimidine-2,4dione,
3-[4-(2-methoxyphenyl)piperazinylethyl]-1-methyl-5-phenylthieno[2,3-d]pyrimidine-2,4-dione,
3-[4-(2-methoxyphenyl)piperazinylethyl]-5-(3-methylphenyl)thieno[2,3-d]pyrimidine-2,4-dione, and
3-[4-(2-methoxyphenyl)piperazinylethyl]-6-phenylthieno[2,3-d]pyrimidine-2,4-dione, or a pharmaceutically acceptable salt, ester or prodrug thereof.

SYNTHETIC METHODS

Abbreviations

Abbreviations which have been used in the descriptions of the scheme and the examples that follow are: DMF for N,N-dimethylformamide, DMSO for dimethyl sulfoxide, and TEA for triethylamine.

Chemistry

The compounds and processes of the present invention will be better understood in connection with the following synthetic schemes which illustrate the methods by which the compounds of the invention may be prepared. The compounds of this invention may be prepared by a variety of synthetic routes. Representative procedures are outlined in Schemes 1–3 where $R_1$, $R_2$, $R_3$, $R_4$, $R_5$, and n are previously defined unless indicated otherwise, Rx is alkyl of one to six carbons, and —E is —CN or —CO$_2$RX. It will be readily apparent to one of ordinary skill in the art reviewing the synthetic route depicted below that other compounds within Formula I and II can be synthesized by the substitution of appropriate reactants and agents in the synthesis shown below.

Scheme 1

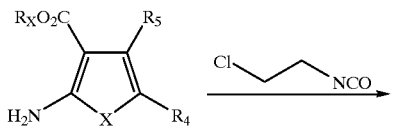

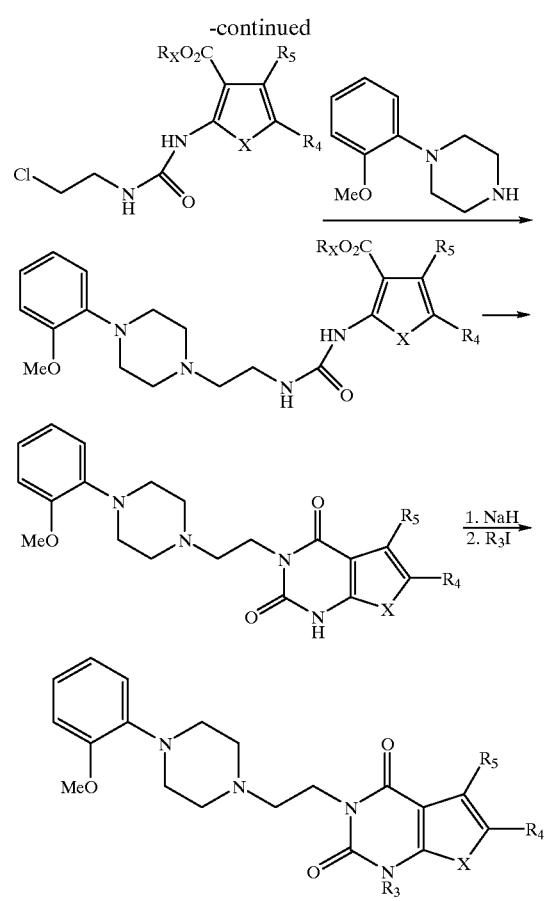

Scheme 1 shows the synthesis of compounds of Formula I and II where $R_3$ is hydrogen or alkyl and X=S. The appropriate 2-aminothiophene was reacted with a chloroalkylisocyanate in a solvent such as toluene with heating to provide a chloroalkylurea. The chloroalkylurea was reacted with o-methoxyphenylpiperazine in acetonitrile with diisopropylethylamine to provide a urea The urea was reacted with potassium t-butoxide in ethyl alcohol to provide compounds of Formula I and II. Reaction of this compound of Formula I with a base such as sodium hydride followed by an alkyl halide provided the N-alkylated compounds of Formula I and II. This method can also be employed to prepare examples where X=O, S, or NH as described in Matsuda, T. et al. *Chem Pharm Bull* 1985,33, 937; Cocco, M. T. et al. *Il Farmaco-Ed. Sc.* 1988, 43, 103; Abdelrazek, F. M. *J. Prakt. Chem.* 1990, 332, 479; and Toja, E. et al. *Synthesis* 1987, 272, each of which is hereby incorporated by reference.

Scheme 2

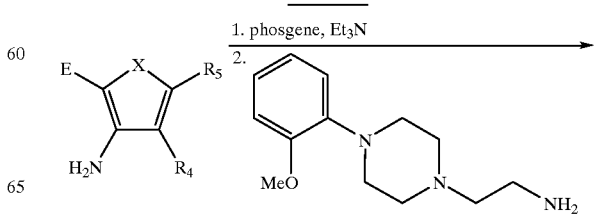

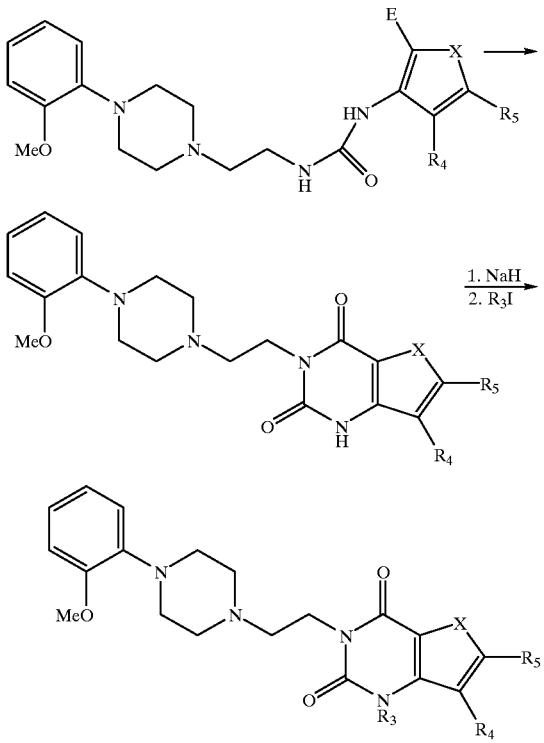

Scheme 2 shows the synthesis of compounds of Formula I and II where R₃ is hydrogen or alkyl and X=NH, S, or O. An appropriately substituted 3-aminothiophene or 3-aminofuran, including but not limited to those described in Gewald, K. et al. *Liebigs Ann. Chem.* 1984, 1702; Hartmann, H. et al. *Synthesis* 1984, 275; and Kirsch, G. et al. *J. Heterocyclic Chem.* 1982, 19, 443, is reacted with phosgene and triethylamine in a solvent such as dichloromethane or tetrahydrofuran to give an intermediate isocyanate that is reacted with an aminoalkylpiperazine to give a urea. The urea is cyclized with a base such as potassium t-butoxide in ethyl alcohol to provide compounds of Formula I and II. Reaction of compounds of Formula I and II with a base such as sodium hydride followed by an alkyl halide provides the N-alkylated compounds of Formula I and II.

Scheme 3

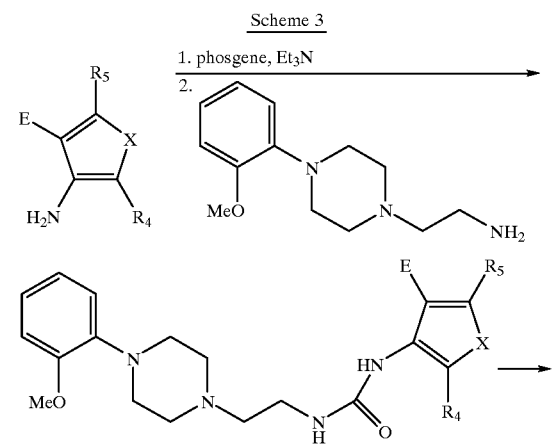

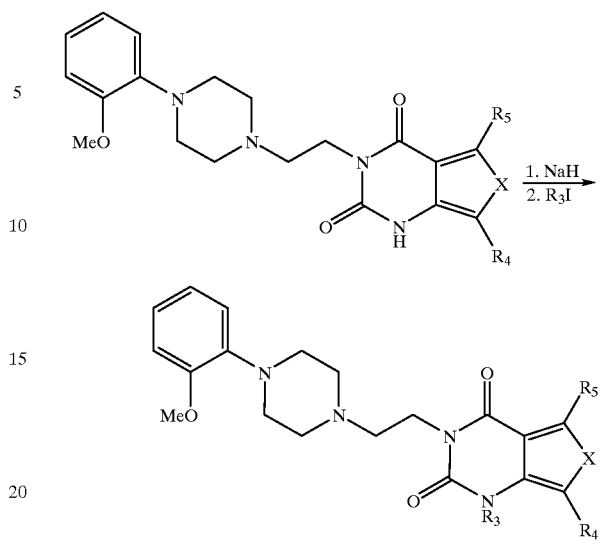

Scheme 3 shows the synthesis of compounds of Formula I and II where R₃ is hydrogen or alkyl, X=S, O, or NH. An appropriately substituted 3-aminothiophene or 3-aminopyrrole, including but not limited to those described in patents U.S. Pat. No. 4,212,806, GB 1587084, and EP 298542, is reacted with phosgene and triethylamine in a solvent such as dichloromethane or tetrahydrofuran to give an intermediate isocyanate that is reacted with the aminoalkylpiperazine to give a urea. The urea is cyclized with a base such as potassium t-butoxide in ethyl alcohol to provide compounds of Formula I and II. Reaction of this compound of Formula I with a base such as sodium hydride followed by an alkyl halide provides the N-alkylated compounds of Formula I and II.

Depending on the nature of R₁, R₂, R₃, R₄, R₅, —E, n, and —CO₂RX, protection and subsequent deprotection of other reactive groups can be required to successfully complete the described synthetic sequences. Commonly used protecting groups are disclosed in Greene and Wuts, "Protective Groups In Organic Synthesis," Second Edition (John Wiley & Sons, New York (1981)), hereby incorporated by reference.

The compounds and processes of the present invention will be better understood in connection with the following examples that are intended as an illustration of and not a limitation upon the scope of the invention as defined in the appended claims.

EXAMPLE 1

3-[4-2-methoxyphenyl)piperazinylethyl]-5-phenylthieno[2,3-d]pyrimidine-2,4-dione

EXAMPLE 1A

N-(3-carboethoxy-4-phenylthien-2-yl)-N'-(chloroethyl)urea

A solution of 2-amino-3-carboethoxy-4-phenylthiophene, prepared by the method of Gewald *Chem. Ber.* (1966), 99, 94, (2.47 g, 0.010 mol) in toluene (30 mL) was heated to reflux, treated with 2-chloroethylisocyanate (1.0 mL, 0.012 mol), stirred for 1 hour, treated with a second portion of 2-chloroethylisocyanate (1.0 mL, 0.012 mol), stirred for 1 hour, cooled, and concentrated. The product was crystallized from ethyl acetate/hexane to provide 2.93 g (83%) yield of the title compound.

$^1$H NMR (300 MHz, CDCl$_3$) δ 0.90 (t, 3H), 3.68 (m, 4H), 4.04 (q, 2H), 5.25 (br s, 1H), 6.48 (s, 1H), 7.30 (m, 5H), 10.69 (br s, 1H).

EXAMPLE 1B

N-(3-carboethoxy4-phenylthien-2-yl)-N'-[2-[4-(2-methoxyphenyl)piperazin-1-yl]ethyl]-urea Example 1A (1.0 g, 2.8 mmol) and 1-(2-methoxyphenyl)piperazine and diisopropylethylamine (0.65 mL) in acetonitrile (20 mL) were heated to reflux for 16 hours treated with water, and extracted with ethyl acetate. The extract was washed with brine, dried (Na$_2$SO$_4$), filtered and concentrated. Purification of the residue on silica gel with 50–75% ethyl acetate/hexane provided 0.70 g of the title compound.

EXAMPLE 1C

3-[4-(2-methoxyphenyl)piperazinylethyl]-5-phenylthieno[2,3-d]pyrimidine-2,4-dione Example 1B (0.70 g, 1.4 mmol) in ethanol (10 mL) was treated with potassium t-butoxide (0.185 g, 1.6 mmol), heated to reflux for 2 hours, cooled, treated with pH 7 buffer solution (75 mL), and extracted with ethyl acetate. The extract was washed with brine, dried (Na$_2$SO$_4$), filtered, concentrated, treated with methanesulfonic acid (0.287 g), and concentrated. The product was recrystallized from ethanol/diethyl ether to provide 0.59 g of the title compound as the methanesulfonate salt $^1$H NMR (300 MHz, DMSO-d$_6$) δ 2.30 (s, 3H), 2.87 (br t, 2H), 3.24 (br q, 2H), 3.52 (br m, 4H), 3.78 (br m, 2H), 3.80 (s, 3H), 4.21 (br t, 2H), 6.97 (m, 4H), 7.10 (s, 1H), 7.39 (m, 3H), 7.50 (m, 2H), 9.10 (br s, 1H), 12.5 (br s, 1H);

MS (DCI/NH$_3$) m/z 463 (M+H)$^+$;

Anal. calcd for C$_{25}$H$_{26}$N$_4$O$_3$S.CH$_4$O$_3$S.0.5H$_2$O: C, 55.01; H, 5.50; N, 9.87. Found: C, 54.90; H, 5.42; N, 9.84.

EXAMPLE 2

3-[4-(2-Methoxyphenyl)piperazinylethyl]-6-methyl-5-phenylthieno[2,3-d]pyrimidine-2,4-dione

EXAMPLE 2A

N-(3-carboethoxy-5-methyl-4-phenylthien-2-yl)-N'-(chloroethyl)urea

A solution of 2-amino-3-carboethoxy-5-methyl-4-phenylthiophene, prepared by the method of Gewald, (5.22 g, 0.020 mol) in toluene (50 mL) was processed as in Example 1A. The product was recrystallized from ethyl acetate/hexane to provide 5.94 g (81%) of the title compound as a white solid.

$^1$H NMR (300 MHz, CDCl$_3$) δ 0.78 (t, 3H), 2.11 (s, 3H), 3.69 (m, 4H), 3.93 (q, 2H), 5.30 (br s, 1H), 7.15 (dd, 2H), 7.33 (m, 3H), 10.65 (br s, 1H).

EXAMPLE 2B

N-(3-carboethoxy-5-methyl-4-phenylthien-2-yl)-N'-[2-[4-(2-methoxyphenyl)piperazin-1-yl]ethyl]-urea A solution of Example 2A (0.60 g, 1.6 mmol), 1-(2-methoxyphenyl)piperazine (0.84 g, 6.5 mmol) and diisopropylethylamine (0.35 mL) in acetonitrile (25 mL) was processed as in Example 1B. Purification of the crude product on silica gel with 2% triethylamine 50% ethyl acetate/hexane provided 0.53 g of the title compound.

EXAMPLE 2C

3-[4-(2-methoxyphenyl)piperazinylethyl]-6-methyl-5-phenylthieno[2,3-d]pyrimidine-2,4-dione Example 2B (0.53 g, 1.0 mmol) and potassium t-butoxide (0.136 g, 1.2 mmol) in ethanol (10 mL) was processed as in Example 1C to provide 0.37 g of the title compound as the methanesulfonate salt $^1$H NMR (300 MHz, DMSO-d$_6$) δ 2.22 (s, 3H), 2.30 (s, 3H), 2.85 (br t, 2H), 3.22 (br q, 2H), 3.43 (br m, 2H), 3.54 (br d, 2H), 3.76 (br d, 2H), 3.79 (s, 3H), 4.17 (br t, 2H), 6.96 (m, 4H), 7.29 (m, 2H), 7.39 (m, 3H), 9.10 (br s, 1H), 12.4 (br s, 1H);

MS (DCI/NH$_3$) m/z 477 (M+H)$^+$;

Anal. calcd for C$_{26}$H$_{28}$N$_4$O$_3$S.CH$_4$O$_3$S:C, 56.63; H, 5.63; N, 9.78. Found: C, 56.66 H, 5.59; N, 9.60.

EXAMPLE 3

3-[4-(2-methoxyphenyl)piperazinylethyl]-1-methyl-5-phenylthieno[2,3-d]pyrimidine-2,4-dione A solution of Example 1C (0.37 g, 0.80 mmol) in DMF (8 mL) was treated sequentially with 80% sodium hydride (26 mg, 0.88 mmol) and methyl iodide (0.050 mL, 0.80 mmol), stirred 3 hours, quenched in water, and extracted with ethyl acetate. The extract was washed with brine, dried (Na$_2$SO$_4$), filtered and concentrated. Purification of the residue on silica gel with 25–50% ethyl acetate/hexane followed by treatment with methanesulfonic acid (2 equiv) in ethyl acetate (40 mL) and ethanol (10 mL) provided 0.36 g of the title compound as the bis methanesulfonate salt $^1$H NMR (300 MHz, DMSO-d$_6$) δ 2.35 (s, 6H), 2.89 (br t, 2H), 3.25 (br m, 2H), 3.51 (br m, 2H), 3.55 (s, 3H), 3.55 (br m, 2H), 3.78 (br d, 2H), 3.80 (s, 3H), 4.27 (br t, 2H), 6.97 (m, 4H), 7.22 (s, 1H), 7.40 (m, 3H), 7.50 (m, 2H), 9.18 (br s, 1H);

MS (DCI/NH$_3$) m/z 477 (M+H)$^+$;

Anal. calcd for C$_{26}$H$_{28}$N$_4$O$_3$S.2CH$_4$O$_3$S.0.5H$_2$O: C, 49.62; H, 5.50; N, 8.27. Found: C, 49.72; H, 5.55; N, 8.20.

EXAMPLE 4

3-[4-(2-methoxyphenyl)piperazinylethyl]-5-(3-methylphenyl)thieno[2,3-d]pyrimidine-2,4-dione

EXAMPLE 4A

N-[3-carboethoxy-4-(3-methylphenyl)thien-2-yl]-N'-(chloroethyl)urea

A solution of 2-amino-3-carboethoxy-4-(3-methylphenyl)thiophene, prepared by the method of Gewald, (4.0 g, 0.015 mol) in toluene (50 mL) was processed as in Example 1A. Purification of the residue on silica gel with 10–25% ethyl acetate/hexane provided the title compound.

$^1$H NMR (300 MHz, CDCl$_3$) δ 0.93 (t, 3H), 2.37 (s, 3H), 3.70 (m, 4H), 4.05 (q, 2H), 5.44 (br s, 1H), 6.49 (s, 1H), 7.11 (m, 3H), 7.21 (t, 1H), 10.70 (br s, 1H).

EXAMPLE 4B

N-[3-carboethoxy-4-(3-methylphenyl)thien-2-yl]-N'-[2-[4-(2-methoxyphenyl)piperazin-1-yl]ethyl]-urea Example 4A (1.0 g, 2.7 mmol), 1-(2-methoxyphenyl)piperazine (0.68 g, 3.5 mmol), diisopropylethylamine (0.62 mL) in acetonitrile (20 mL) was processed as in Example 1B. Purification of the crude product on silica gel with ethyl acetate provided 1.02 g of the title compound.

EXAMPLE 4C

3-[4-(2-Methoxyphenyl)piperazinylethyl]-5-(3-methylphenyl)thieno[2,3-d]pyrimidine-2,4-dione Example 4B (1.02 g, 1.95 mmol) and potassium t-butoxide (0.24 g, 2.2 mmol) in ethanol were treated according to Example 1C to provide 0.302 g of the title compound as the bis methanesulfonate salt $^1$H NMR (300 MHz, DMSO-$d_6$) δ2.34 (s, 3H), 2.35 (s, 6H), 2.88 (br t, 2H), 3.24 (br q, 2H), 3.49 (br m, 2H), 3.56 (br d, 2H), 3.80 (br d, 2H), 3.80 (s, 3H), 4.21 (br t, 2H), 6.96 (m, 4H), 7.06 (s, 1H), 7.17 (m, 1H), 7.30 (m, 3H), 9.11 (br s, 1H), 12.5 (br s, 1H);

MS (DCI/NH$_3$) m/z 477 (M+H)$^+$;

Anal. calcd for $C_{26}H_{28}N_4O_3S \cdot 2CH_4O_3S \cdot H_2O$: C, 48.97; H, 5.58; N, 8.16. Found: C, 49.27; H, 5.65; N, 8.03.

EXAMPLE 5

3-[4-(2-Methoxyphenyl)piperazinylethyl]-6-phenylthieno[2,3-d]pyrimidine-2,4-dione

EXAMPLE 5A

N-(3-carboethoxy-5-phenylthien-2-yl)-N'-(chloroethyl)urea

A solution of 2-amino-3-carboethoxy-5-phenylthiophene, prepared by the method of Gewald, (0.68 g, 3.1 mmol) in toluene (6 mL) was processed as in Example 1A. Purification the crude product on silica gel with 25% ethyl acetate/hexane provided 806 mg (79%) of the title compound as a foam.

EXAMPLE 5B

N-(3-carboethoxy-5-phenylthien-2-yl)-N'-[2-[4-(2-methoxyphenyl)piperazin-1-yl]ethyl]-urea A solution of Example 5A (462 mg, 1.37 mmol), 1-(2-methoxyphenyl)piperazine (1.7 mmol), diisopropylethylamine (0.29 mL) in acetonitrile (5 mL) was processed as in Example1B. Purification of the residue on silica gel with ethyl acetate provided 282 mg (41%) of the title compound.

EXAMPLE 5C

3-[4-(2-methoxyphenyl)piperazinylethyl]-6-phenylthieno[2,3-d]pyrimidine-2,4-dione A solution of Example 5B (387 mg, 0.762 mmol) in ethanol (5 mL) was treated with 1M potassium t-butoxide/THF (0.84 mL), heated to reflux for 90 minutes, cooled, quenched with 1N HCl (0.84 mL), and partitioned between water and ethyl acetate. The insoluble solid was collected, washed with ethyl acetate, slurried in methanol, treated with methanesulfonic acid (2 equiv), and concentrated. The product was crystallized from ethanol to provide 180 mg the title compound as the bis methanesulfonate salt.

$^1$H NMR (300 MHz, DMSO-$d_6$) δ2.32 (S, 6H), 2.90 (br t, 2H), 3.28 (br q, 2H), 3.55 (br m, 4H), 3.80 (m, 2H), 3.80 (s, 3H), 4.27 (br t, 2H), 6.98 (m, 4H), 7.34 (t, 1H), 7.44 (t, 2H), 7.66 (s, 1H), 7.70 (d, 2H), 9.12 (br s, 1H), 12.5 (br s, 1H);

MS (DCI/NH$_3$) m/z 463 (M+H)$^+$;

Anal. calcd for $C_{27}H_{34}N_4O_9S_3 \cdot 5H_2O$: C, 47.56; H, 5.47; N, 8.22. Found: C, 47.36; H, 5.47; N, 8.04.

Examples 6 through 15 may be prepared according to the procedures described in Examples 1 through 5 and the synthetic schemes and discussions contained herein.

EXAMPLE 6

3-[2-[4-(2-methoxyphenyl)-1-piperazinyl]ethyl]-5-phenylfuro[2,3-d]pyrimidine-2,4(1H,3H)-dione

EXAMPLE 7

3-[2-[4-(2-methoxyphenyl)-1-piperazinyl]ethyl]-5-phenyl-1H-pyrrolo[2,3-d]pyrimidine-2,4(3H,7H)-dione

EXAMPLE 8

3-[2-[4-(2-methoxyphenyl)-1-piperazinyl]ethyl]-5-phenylfuro[2,3-d]pyrimidine-2,4(1H,3H)-dione

EXAMPLE 9

3-[2-[4-(2-methoxyphenyl)-1-piperazinyl]ethyl]-6-phenyl-1H-pyrrolo[2,3-d]pyrimidine-2,4(3H,7H)-dione

EXAMPLE 10

3-[2-[4-(2-methoxyphenyl)-1-piperazinyl]ethyl]-7-phenyl[3,4-d]pyrimidine-2,4(1H,6H)-dione

EXAMPLE 11

3-[2-[4-(2-methoxyphenyl)-1-piperazinyl]ethyl]-7-phenylthieno[3,4-d]pyrimidine-2,4(1H,3H)-dione

EXAMPLE 12

3-[2-[4-(2-methoxyphenyl)-1-piperazinyl]ethyl]-5-phenylthieno[3,4-d]pyrimidine-2,4(1H,3H)-dione

EXAMPLE 13

3-[2-[4-(2-methoxyphenyl)-1-piperazinyl]ethyl]-7-phenylfuro[3,2-d]pyrimidine-2,4(1H,3H)-dione

EXAMPLE 14

3-[2-[4-(2-methoxyphenyl)-1-piperazinyl]ethyl]-6-phenylthieno[3,2-d]pyrimidine-2,4(1H,3H)-dione

EXAMPLE 15

3-[2-[4-(2-methoxyphenyl)-1-piperazinyl]ethyl]-7-phenylthieno[3,2-d]pyrimidine-2,4(1H,3H)-dione It is to be understood that the foregoing detailed description and accompanying examples are merely illustrative and are not to be taken as limitations upon the scope of the invention that is defined solely by the appended claims and their equivalents. Various changes and modifications to the disclosed embodiments will be apparent to those skilled in the art. Such changes and modifications, including without limitation those relating to the chemical structures, substituents, derivatives, intermediates, syntheses, formulations, and/or methods of use of the invention, may be made without departing from the spirit and scope thereof.

Determination of Biological Activity
In vitro Binding Assays

For purposes of discussing $\alpha_1$-adrenoceptor subtypes, the IUPHAR convention of using lower case letters to define molecular clones and upper case letters to indicate pharmacologically defined adrenoceptors has been followed. Also, the newly recommended nomenclature for alpha-1 ($\alpha_{1a}$, $\alpha_{1b}$, $\alpha_{1d}$) is used.

Representative compounds of the invention were evaluated for α-adrenoceptor binding affinity in vitro using [$^3$H]-prazosin as the radioligand and two cloned $\alpha_1$ adrenoceptors expressed in LTK cells: $\alpha_{1b}$ (hamster), and $\alpha_{1d}$ (rat). Additionally, binding affinity against the pharmacologically defined $\alpha_{1A}$ adrenoceptor (rat submaxillary gland) was measured.

The cDNA clones encoding the α-1 adrenoceptors ($\alpha_{1b}$ and $\alpha_{1d}$) were obtained from TULCO (Triangle Universities Licensing Consortium, Research Triangle Park, N.C.) and inserted into the eukaryotic expression vector SnaB30. In this vector, expression of the adrenoceptor gene is under the transcriptional control of an SV40 early promoter. Positive drug selection is provided by a neomycin-resistance gene. Mouse fibroblast cells (LTK) were transfected with the $\alpha_1$ expression plasmids and grown in Dulbecco's modified Eagle's medium (DMEM) containing 10% fetal calf serum and 30 mM G418. Stable G418-resistant parental lines were generated and successful expression of adrenoceptor protein was monitored using radioligand binding techniques. Stable single cell clones derived from the parental lines were screened in adrenoceptor binding assays to identify clones having high adrenoceptor density. Roller bottle cultures of the cloned lines were used to provide cell membranes for subsequent adrenoceptor binding characterization studies. A cell line containing the SnaB30 vector expressing the human erythropoietin gene served as a negative control.

For adrenoceptor binding assays, large scale membrane preparations were utilized in which 6 million cells were seeded into small (450 cm$^2$) Corning tissue culture roller bottles. 200 mL of DMEM containing 10% fetal calf serum and 300 mM G418 were added to each roller bottle. A 95% air/5% CO$_2$ gas mixture (sterile) was injected into each roller bottle prior to sealing. The bottles were incubated at 37° C. on a roller rack for 5 days. Cells were re-fed with fresh medium after 3 days in culture.

On the fifth day of culture, growth medium was removed from cells grown in the roller bottles, and the cells were washed twice with PBS (Sigma, 120 mM NaCl, 2.7 mM KCl, 10 mM Na$_2$HPO$_4$—NaH$_2$PO$_4$, pH=7.4). Cells were detached from the roller bottles by incubating for 15 minutes at 37° C. in a Tris-EDTA solution (10 mM Tris, 100 mM NaCl, 1 mM EDTA, pH=7.4). The cell suspension from each roller bottle was decanted into preweighed centrifuge tubes and kept on ice. An aliquot of each cell suspension was generally taken for cell counting. Cells were centrifuged at 3000×G for 5 min at 2–4° C., washed with PBS and recentrifuged. The supernatant was decanted and the pellet was weighed to determine the wet weight of cells. Cells were washed a final time in 40 vol 5 mM Tris-HCl, 5 mM EDTA, pH=7.7, centrifuged at 40,000×G for 10 minutes, homogenized in 10 mL of 50 mM Tris-HCl, 5 mM EDTA (pH=7.4), and diluted to 40 mL/tube. Homogenates were centrifuged at 40,000×G for 10 minutes. The supernatant was decanted and the pellets were rehomogenized in 50 mM Tris-HCl (pH=7.4) and centrifuged as before. The supernatant was decanted, the homogenate was resuspended in 6.25 volumes (per gram wet weight) of 50 mM Tris-HCl, and aliquots of the pooled homogenates were frozen in liquid nitrogen and stored at −70° C. until the time of assay. Rat submaxillary glands were used for $\alpha_{1A}$ adrenoceptors and were prepared essentially as described (Michel, A. D., Loury, D. N. and Whiting, R. L., Brit. J. Pharmacol. 98: 83–889 (1989)), hereby fully incorporated by reference.

Receptor binding assays for a-I adrenoceptors were performed essentially as described by Greengrass and Bremner (Eur. J. Pharmacol. 55: 323–326 (1979)). Briefly, plastic Bioblocks™ (DBM Scientific, Valencia, Calif.) were incubated at 25° C. for 50 minutes with 500 mL of membrane homogenate (diluted with an additional 96 volumes (for cloned adrenoceptors, 12 volumes for submaxillary gland)) in 50 mM Tris-HCl buffer (pH=7.7 at the time of assay), 450 mL of [$^3$H]prazosin (0.2 nM final concentration, 75–85 Ci/mmole, DuPont-NEN Corp., Boston, Mass.), and 50 mL of either water (for total binding) or 10 mM phentolamine (final concentration, for non-specific binding). Following equilibration, bound radioligand was separated from free on GF/B filters (presoaked in 0.5% polyethyleneamine) using either a Brandel or Packard cell harvester. Radioactivity was determined by standard liquid scintillation techniques. Data were analyzed as previously described (Hancock, A. A., Kyncl, J. J., Martin, Y. C. and DeBernardis, J. F., J. Receptor Res. 8: 23–46 (1988)).

Table 1 presents receptor binding assay values for compounds of the present invention as compared to known nonselective, $\alpha_1$ adrenoceptor antagonists terazosin and tamsulosin. The results show that the compounds of the present invention bind to the $\alpha_1$-adrenoceptor and show specificity for the $\alpha_{1d}$ adrenoceptor.

TABLE 1

| | Radioligand Binding Ki (nM) | | |
|---|---|---|---|
| Example | $\alpha_{1A}$ (Rat) | $\alpha_{1b}$ (Hamster) | $\alpha_{1d}$ (Rat) |
| terazosin | 0.823 | 0.689 | 1.01 |
| tamsulosin | 0.028 | 0.204 | 0.068 |
| 1 | 2.43 | 3.41 | 0.213 |
| 2 | 1.97 | 2.44 | 0.251 |
| 3 | 2.62 | 4.47 | 0.710 |
| 4 | 3.47 | 2.74 | 0.170 |
| 5 | 0.578 | 1.86 | 0.361 |

In Vivo Determination of Intraurethral Pressure (IUP) in Canines

The intraurethral pressure (IUP) model in aged canines is an accepted model of measuring the effect of prostate smooth muscle contraction on urethral tone. Canines also have an enclosed prostate covering the urethral shaft and thus provide an anatomical correlate with humans.

Beagle dogs (Marshall Farms) greater that 2 years of age and weighing between 12 and 15 kg were pre-anesthetized with thiopental sodium 15 mg/kg i.v. (Pentothal™, Abbott Laboratories, Abbott Park, Ill.) then placed under general anesthesia (isoflurane). A 7F Swan-Ganz balloon catheter (Multiflex-list no. 41224-01, Abbott) was lubricated with a water soluble jelly, inserted into the urethral orifice and advanced approximately 40 cm in male dogs (considerably less in females) until the balloon tip was placed well inside the bladder. The balloon was then inflated with 1 mL of room air, and the catheter was slowly withdrawn just past the first resistance that is felt at the bladder neck. Preliminary experiments in which dogs were sacrificed after such placement confirmed that this technique results in consistent positioning of the balloon within the prostatic urethra in males or the corresponding location in females. The balloon port of the catheter was connected to a Gould Statham P23Dd pressure transducer interfaced to a computerized data acquisition system (Modular Instruments, Inc., Malvern, Pa.) for the measurement of intraurethral pressure (IUP).

Dogs were then treated with propranolol to block the β-adrenoceptor agonist effects of test agonists. Dose-response curves of the intraurethral pressor effect of epinephrine (EPI) were obtained before and after each of up to 3 increasing doses of a test antagonist (i.v.). Fifteen minutes were allowed after each antagonist dose for equilibration before the next agonist dose-response was initiated. The increase in IUP caused by a given agonist dose was allowed to return to baseline before the next dose was given. The estimated antagonist dissociation constant (in vivo pseudo $pA_2$) was determined by Schild analysis (Brune, et al., Drug Development Research, 34:267–275 (1995).

The results are shown in Table 2. The results indicate that the compounds of the invention inhibit EPI induced increases in IUP.

TABLE 2

Inhibition of EPI Induced Increase in Canine IUP

| Example | IUP (pA2) |
| --- | --- |
| terazosin | 6.97 |
| tamsulosin | 8.91* |
| 1 | 7.95 |
| 5 | 8.47 |

*add 0.4 if slope adjusted to 1

Spontaneously Hypertensive Rat (SHR) Model

The SHR model historically has been used as a predictor for the hypotensive effects of $\alpha_1$ adrenoceptor antagonists. Male spontaneously hypertensive rats were anesthetized, and the left femoral artery and vein were catheterized for the measurement of mean arterial pressure (MAP) and drug administration respectively. The arterial catheter was connected to a Gould Statham p23ID transducer and the pressure waveform was recorded. MAP (mm Hg) and heart rate (HR, beats/min.) were determined on-line using a BUXCO Cardiovascular Analyzer. After a 30 minute pre-dose control period, each rat was given one dose of a test antagonist i.v., and the MAP and HR were monitored for an additional 2.5 hours. The area under the hypotensive response curve up to 60 minutes post dosing ($T_{60}$ AUC) was determined using a trapezoidal rule integration of the percent change from control arterial pressure dataset. The results are expressed as a $pED_{50}$ value, which is defined as the negative log of the dose that produced a hypotensive response of −1250, which constitutes 50% of the area under the curve between SHR and normotensive rats.

The results are shown in Table 3. The results show that the compounds of the invention possess hypotensive activity and can be useful for treatment of hypertension.

TABLE 3

Spontaneously Hypertensive Rat (SHR) Activity

| Example | $pED_{50}$ |
| --- | --- |
| terazosin | 6.40 |
| tamsulosin | 7.22 |
| 1 | 6.17 |
| 5 | 6.04 |

Pharmaceutical Compositions and Methods of Treatment

The present invention also provides pharmaceutical compositions which comprise compounds of the present invention formulated together with one or more non-toxic pharmaceutically acceptable carriers. The pharmaceutical compositions may be specially formulated for oral administration in solid or liquid form, for parenteral injection, or for rectal administration.

The pharmaceutical compositions of this invention can be administered to humans and other animals orally, rectally, parenterally, intracisternally, intravaginally, intraperitoneally, topically (as by powders, ointments, or drops), bucally, or as an oral or nasal spray. The term "parenteral" administration as used herein refers to modes of administration which include intravenous, intramuscular, intraperitoneal, intrasternal, subcutaneous and intraarticular injection and infusion.

Pharmaceutical compositions of this invention for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol, and the like), and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants.

These compositions may also contain adjuvants such as preservative, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents such as sugars, sodium chloride, and the like, Prolonged absorption of the injectable pharmaceutical form may be brought about by the inclusion of agents which delay absorption such as aluminum monostearate and gelatin.

In some cases, in order to prolong the effect of the drug, it is desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides) Depot injectable formulations are also prepared by entrapping the drug in liposomes or microemulsions which are compatible with body tissues.

The injectable formulations can be sterilized, for example, by filtration through a bacterial-retaining filter, or by incorporating sterilizing agents in the form of sterile solid compositions which can be dissolved or dispersed in sterile water or other sterile injectable medium just prior to use.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, and tragacanth, and mixtures thereof.

Compositions for rectal or vaginal administration are preferably suppositories which can be prepared by mixing the compounds of this invention with suitable non-irritating excipients or carriers such as cocoa butter, polyethylene glycol or a suppository wax which are solid at room temperature but liquid at body temperature and therefore melt in the rectum or vaginal cavity and release the active compound.

Compounds of the present invention can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients, and the like. The preferred lipids are the phospholipids and the phosphatidyl cholines (lecithins), both natural and synthetic.

Methods to form liposomes are known in the art. See, for example, Prescott, Ed., *Methods in Cell Biology,* Volume XIV, Academic Press, New York, N.Y. (1976), p. 33 et seq.

Dosage forms for topical administration of a compound of this invention include powders, sprays, ointments and inhalants. The active compound is mixed under sterile conditions with a pharmaceutically acceptable carrier and any needed preservatives, buffers, or propellants which may be required. Opthalmic formulations, eye ointments, powders and solutions are also contemplated as being within the scope of this invention.

Actual dosage levels of active ingredients in the pharmaceutical compositions of this invention may be varied so as to obtain an amount of the active compound(s) that is effective to achieve the desired therapeutic response for a particular patient, compositions, and mode of administration. The selected dosage level will depend upon the activity of the particular compound, the route of administration, the severity of the condition being treated, and the condition and prior medical history of the patient being treated. However, it is within the skill of the art to start doses of the compound at levels lower than required for to achieve the desired therapeutic effect and to gradually increase the dosage until the desired effect is achieved.

Generally dosage levels of about 1 to about 50, more preferably of about 5 to about 20 mg of active compound per kilogram of body weight per day are administered orally to a mammalian patient. If desired, the effective daily dose may be divided into multiple doses for purposes of administration, e.g. two to four separate doses per day.

Compounds of the present invention may be utilized as providing a method of treating benign prostatic hyperplasia, hypertension, detrusor instability, and incontinence comprising administering a therapeutically effective amount of a compound of Formula I or II, or a phamaceutically acceptable salt, ester or prodrug thereof.

Compounds of the present invention may be utilized by providing a method of anatgonizing alpha-1D adrenoceptors in a comprising administering a therapeutically effective amount of a compound of Formula I or II, or a phamaceutically acceptable salt, ester or prodrug thereof.

Compounds of the present invention may be formulated into a pharmaceutical composition comprising a compound of Formula I or II, or a phamaceutically acceptable salt, ester or prodrug thereof, and a pharmaceutically acceptable carrier.

What is claimed is:

1. A compound having Formula I

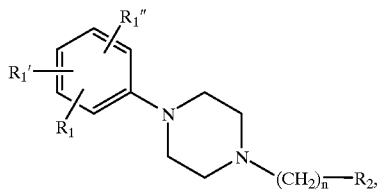

or a pharmaceutically acceptable salt thereof, wherein $R_1$, $R_{1'}$, and $R_{1''}$ are independently selected from the group consisting of (a) halo, (b) hydroxy, (c) nitro, (d) amino, (e) N-protected amino, (f) haloalkoxy, (g) perfluoroalkoxy, (h) carboxy, (i) O-protected carboxy, (j) cycloalkoxy, (k) cycloalkyl, (l) cycloalkylalkyl, (m) alkoxy, (n) alkyl, (o) alkenyl, (p) alkenyloxy, (q) alkynyloxy, (r) alkynyl, (s) alkoxycarbonyl, and (t) hydrogen wherein (j)–(s) can be optionally substituted with 1, 2, or 3 substituents independently selected from the group consisting of alkoxy, hydroxy, carboxy, amino, halo, hydroxy, and nitro;

n is 2–10; and $R_2$ is

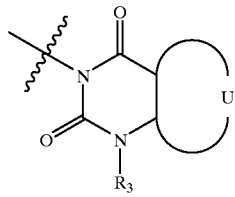

wherein U, taken together with the carbon atoms to which it is attached, forms a ring selected from the group consisting of (a) a mono- or disubstituted five-membered heterocycle having four carbon atoms, two double bonds, and one heteroatom selected from the group consisting of —N($R_5$)—, —O—, and —S— wherein $R_5$ is hydrogen, alkyl, alkenyl, alkynyl, cycloalkyl, cycloalkylalkyl, aryl, arylalkyl, heterocycle, and (heterocyclic)alkyl, and the mono- or di- substituents are independently selected from the group consisting of hydrogen, alkyl, alkenyl, alkynyl, cycloalkyl, cycloalkylalkyl, aryl, arylalkyl, heterocycle, and (heterocyclic)alkyl, with the proviso that at least one of $R_5$, mono-, or di- substituents is cycloalkyl, cycloalkylalkyl, aryl, arylalkyl, heterocyclic, or (heterocyclic)alkyl; and wherein $R_3$ is selected from the group consisting of hydrogen, alkyl, alkenyl, alkynyl, cycloalkyl, and cycloalkylalkyl.

2. A compound according to claim 1 wherein U is

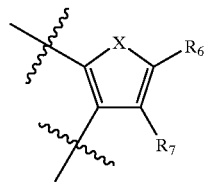

wherein X is selected from the group consisting of —N($R_5$)—, —O—, and —S—, wherein $R_5$, $R_6$ and $R_7$ are independently selected from the group consisting of hydrogen, alkyl, alkenyl, alkynyl, cycloalkyl, cycloalkylalkyl, aryl, arylalkyl, heterocycle, and (heterocyclic)alkyl, with the proviso that at least one of $R_5$, $R_6$ and $R_7$ cycloalkyl, cycloalkylalkyl, aryl, arylalkyl, heterocyclic, or (heterocyclic)alkyl; or a pharmaceutically acceptable salt thereof.

3. A compound according to claim 2 wherein X is selected from the group consisting of —N($R_5$)—, —O—, and —S—, n is 2–5, $R_3$ is hydrogen or alkyl, $R_1$, $R_{1'}$, and $R_{1''}$ are independently selected from hydrogen and alkoxy, and $R_5$, $R_6$ and $R_7$ are independently hydrogen or aryl with the proviso that at least one of $R_5$, $R_6$ and $R_7$ is aryl; or a pharmaceutically acceptable salt thereof.

4. A compound or a pharmaceutically acceptable salt thereof according to claim 1, wherein U is

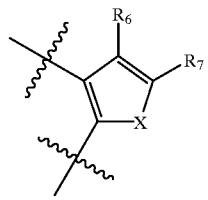

wherein $R_5$, $R_6$ and $R_7$ are independently selected from the group consisting of hydrogen, alkyl, alkenyl, alkynyl, cycloalkyl, cycloalkylalkyl, aryl, arylalkyl, heterocycle, and (heterocyclic)alkyl, with the proviso that at least one of $R_5$, $R_6$ and $R_7$ is cycloalkyl, cycloalkylalkyl, aryl, arylalkyl, heterocyclic, or (heterocyclic)alkyl.

5. A compound according to claim 4 wherein X is selected from the group consisting of —N($R_5$)—, —O—, and —S—, n is 2–5, $R_3$ is hydrogen or alkyl, $R_1$, $R_{1'}$, and $R_{1''}$ are independently selected from hydrogen and alkoxy, and $R_5$, $R_6$ and $R_7$ are independently hydrogen or aryl with the proviso that at least one of $R_5$, $R_6$ and $R_7$ is aryl; or a pharmaceutically acceptable salt thereof.

6. A compound or a pharmaceutically acceptable salt thereof according to claim 1, wherein U is

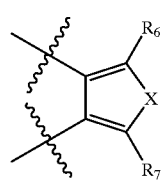

wherein X is selected from the group consisting of —N($R_5$)—, —O—, and —S— wherein $R_5$, $R_6$ and $R_7$ are independently selected from the group consisting of hydrogen, alkyl, alkenyl, alkynyl, cycloalkyl, cycloalkylalkyl, aryl, arylalkyl, heterocycle, and (heterocyclic)alkyl, with the proviso that at least one of $R_5$, $R_6$ and $R_7$ is cycloalkyl, cycloalkylalkyl, aryl, arylalkyl, heterocyclic, or (heterocyclic)alkyl.

7. A compound according to claim 6 wherein X is selected from the group consisting of —N($R_5$)—, —O—, and —S—, n is 2–5, $R_3$ is hydrogen or alkyl, $R_1$, $R_{1'}$, and $R_{1''}$ are independently selected from hydrogen and alkoxy, and $R_5$, $R_6$ and $R_7$ are independently hydrogen or aryl with the proviso that at least one of $R_5$, $R_6$ and $R_7$ is aryl; or a pharmaceutically acceptable salt thereof.

8. A compound or a pharmaceutically acceptable salt thereof selected from the group consisting of
3-[4-(2-methoxyphenyl)piperazinylethyl]-5-phenylthieno[2,3-d]pyrimidine-2,4-dione,
3-[4-(2-methoxyphenyl)piperazinylethyl]-6-methyl-5-phenylthieno[2,3-d]pyrimidine-2,4-dione,
3-[4-(2-methoxyphenyl)piperazinylethyl]-1-methyl-5-phenylthieno[2,3-d]pyrimidine-2,4-dione,
3-[4-(2-methoxyphenyl)piperazinylethyl]-5-(3-methylphenyl)thieno[2,3-d]pyrimidine-2,4-dione, and
3-[4-(2-methoxyphenyl)piperazinylethyl]-6-phenylthieno[2,3-d]pyrimidine-2,4-dione.

9. A compound or a pharmaceutically acceptable salt, ester or prodrug thereof selected from the group consisting of
3-[2-[4-(2-methoxyphenyl)-1-piperazinyl]ethyl]-5-phenylfuro[2,3-d]pyrimidine-2,4(1H,3H)-dione,
3-[2-[4-(2-methoxyphenyl)-1-piperazinyl]ethyl]-5-phenyl-1H-pyrrolo[2,3-d]pyrimidine-2,4(3H,7H)-dione,
3-[2-[4-(2-methoxyphenyl)-1-piperazinyl]ethyl]-5-phenylfuro[2,3-d]pyrimidine-2,4(1H,3H)-dione,
3-[2-[4-(2-methoxyphenyl)-1-piperazinyl]ethyl]-6-phenyl-1H-pyrrolo[2,3-d]pyrimidine-2,4(3H,7H)-dione,
3-[2-[4-(2-methoxyphenyl)-1-piperazinyl]ethyl]-7-phenylthieno[3,4-d]pyrimidine-2,4(1H,3H)-dione,
3-[2-[4-(2-methoxyphenyl)-1-piperazinyl]ethyl]-5-phenylthieno[3,4-d]pyrimidine-2,4(1H,3H)-dione,
3-[2-[4-(2-methoxyphenyl)-1-piperazinyl]ethyl]-7-phenylfuro[3,2-d]pyrimidine-2,4(1H,3H)-dione,
3-[2-[4-(2-methoxyphenyl)-1-piperazinyl]ethyl]-6-phenylthieno[3,2-d]pyrimidine-2,4(1H,3H)-dione, and
3-[2-[4-(2-methoxyphenyl)-1-piperazinyl]ethyl]-7-phenylthieno[3,2-d]pyrimidine-2,4(1H,3H)-dione.

10. A compound having Formula II

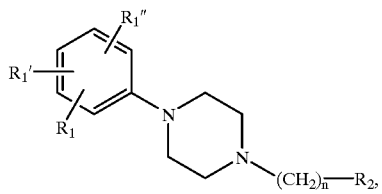

or a pharmaceutically acceptable salt thereof, wherein $R_1$, $R_{1'}$, and $R_{1''}$ are independently selected from the group consisting of (a) halo, (b) hydroxy, (c) nitro, (d) amino, (e) N-protected amino, (f) haloalkoxy, (g) perfluoroalkoxy, (h) carboxy, (i) O-protected carboxy, (j) cycloalkoxy, (k) cycloalkyl, (l) cycloalkylalkyl, (m) alkoxy, (n) alkyl, (o) alkenyl, (p) alkenyloxy, (q) alkynyloxy, (r) alkynyl, (s) alkoxycarbonyl, and (t) hydrogen wherein (j)–(s) can be optionally substituted with 1, 2, or 3 substituents independently selected from the group consisting of alkoxy, hydroxy, carboxy, amino, halo, hydroxy, and nitro;

n is 2–5; and $R_2$ is selected from the group consisting of

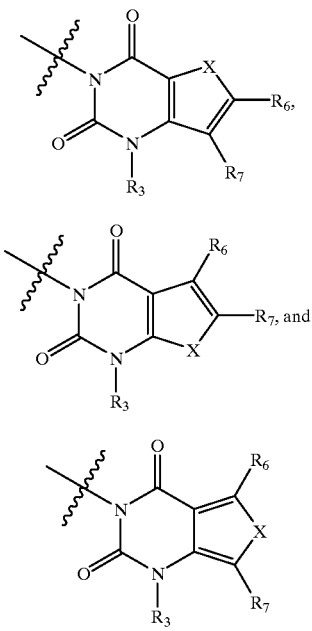

wherein at each occurence X is selected from the group consisting of —N($R_5$)—, —O—, and —S— wherein $R_5$, $R_6$ and $R_7$ are independently selected from the group consisting of hydrogen, alkyl, alkenyl, alkynyl, cycloalkyl, cycloalkylalkyl, aryl, arylalkyl, heterocycle, and (heterocyclic)alkyl, with the proviso that at least one of $R_5$, $R_6$ and $R_7$ is cycloalkyl, cycloalkylalkyl, aryl, arylalkyl, heterocyclic, or (heterocyclic)alkyl, and $R_3$ is selected from the group consisting of hydrogen, alkyl, alkenyl, alkynyl, cycloalkyl, and cycloalkylalkyl.

11. A compound or a pharmaceutically acceptable salt thereof according to claim 10 wherein $R_2$ is

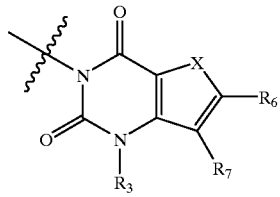

wherein X is selected from the group consisting of —N($R_5$)—, —O—, and —S— wherein $R_5$, $R_6$ and $R_7$ are independently selected from the group consisting of hydrogen, and aryl with the proviso that at least one of $R_5$, $R_6$ and $R_7$ is aryl, and $R_3$ is selected from the group consisting of hydrogen and alkyl.

12. A compound or a pharmaceutically acceptable salt thereof according to claim 10 wherein $R_2$ is

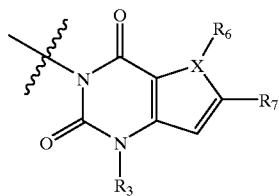

wherein X is selected from the group consisting of —N(R$_5$)—, —O—, and —S— wherein R$_5$, R$_6$ and R$_7$ are independently selected from the group consisting of hydrogen, and aryl with the proviso that at least one of R$_5$, R$_6$ and R$_7$ is aryl, and R$_3$ is selected from the group consisting of hydrogen and alkyl.

13. A compound or a pharmaceutically acceptable salt thereof according to claim 10 wherein R$_2$ is

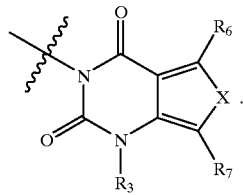

wherein X is selected from the group consisting of —N(R$_5$)—, —O—, and —S— wherein R$_5$, R$_6$ and R$_7$ are independently selected from the group consisting of hydrogen, and aryl with the proviso that at least one of R$_5$, R$_6$ and R$_7$ is aryl, and R$_3$ is selected from the group consisting of hydrogen and alkyl.

14. A compound or a pharmaceutically acceptable salt thereof according to claim 11 wherein R$_1$, R$_{1'}$, and R$_{1''}$ are independently selected from the group consisting of hydrogen and alkoxy, n is 2, X is selected from the group consisting of —N(R$_5$)— and —S— wherein R$_5$, R$_6$ and R$_7$ are independently selected from the group consisting of hydrogen and aryl with the proviso that at least one of R$_5$, R$_6$ and R$_7$ is aryl and R$_3$ is hydrogen or alkyl.

15. A compound or a pharmaceutically acceptable salt thereof according to claim 12 wherein R$_1$, R$_{1'}$, and R$_{1''}$ are independently selected from the group consisting of hydrogen and alkoxy, n is 2, X is selected from the group consisting of —N(R$_5$)— and —S— wherein R$_5$, R$_6$ and R$_7$ are independently selected from the group consisting of hydrogen and aryl with the proviso that at least one of R$_5$, R$_6$ and R$_7$ is aryl and R$_3$ is hydrogen or alkyl.

16. A compound or a pharmaceutically acceptable salt thereof according to claim 13 wherein R$_1$, R$_{1'}$, and R$_{1''}$ are independently selected from the group consisting of hydrogen and alkoxy, n is 2, X is selected from the group consisting of —N(R$_5$)— and —S— wherein R$_5$, R$_6$ and R$_7$ are independently selected from the group consisting of hydrogen and aryl with the proviso that at least one of R$_5$, R$_6$ and R$_7$ is aryl and R$_3$ is hydrogen or alkyl.

17. A pharmaceutical composition comprising a compound of claim 1 and a pharmaceutically acceptable carrier.

18. A pharmaceutical composition comprising a compound of claim 10 and a pharmaceutically acceptable carrier.

19. A pharmaceutical composition comprising a compound of claim 11 and a pharmaceutically acceptable carrier.

20. A pharmaceutical composition comprising a compound of claim 12 and a pharmaceutically acceptable carrier.

21. A pharmaceutical composition comprising a compound of claim 13 and a pharmaceutically acceptable carrier.

22. A method of treating benign prostatic hyperplasia, hypertension, detrusor instability, and incontinence comprising administering to a human a therapeutically effective amount of a compound of claim 1.

23. A method of treating benign prostatic hyperplasia, hypertension, detrusor instability, and incontinence comprising administering to a human a therapeutically effective amount of a compound of claim 10.

24. A method of treating benign prostatic hyperplasia, hypertension, detrusor instability, and incontinence comprising administering to a human a therapeutically effective amount of a compound of claim 11.

25. A method of treating benign prostatic hyperplasia, hypertension, detrusor instability, and incontinence comprising administering to a human a therapeutically effective amount of a compound of claim 12.

26. A method of treating benign prostatic hyperplasia, hypertension, detrusor instability, and incontinence comprising administering to a human a therapeutically effective amount of a compound of claim 13.

27. A method of anatgonizing alpha-1D adrenoceptors in a comprising administering to a human a therapeutically effective amount of a compound of claim 1.

28. A method of anatgonizing alpha-1D adrenoceptors in a comprising administering to a human a therapeutically effective amount of a compound of claim 10.

29. A method of anatgonizing alpha-1D adrenoceptors in a comprising administering to a human a therapeutically effective amount of a compound of claim 11.

30. A method of anatgonizing alpha-1D adrenoceptors in a comprising administering to a human a therapeutically effective amount of a compound of claim 12.

31. A method of anatgonizing alpha-1D adrenoceptors in a comprising administering to a human a therapeutically effective amount of a compound of claim 13.

* * * * *

UNITED STATES PATENT AND TRADEMARK OFFICE
CERTIFICATE OF CORRECTION

PATENT NO. : 6,153,614  
DATED : November 28, 2000  
INVENTOR(S) : Michael D. Meyer et al.

Page 1 of 1

It is certified that error appears in the above-identified patent and that said Letters Patent is hereby corrected as shown below:

Column 33,
Lines 1-10, replace " 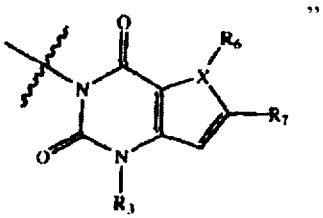 "

with -- 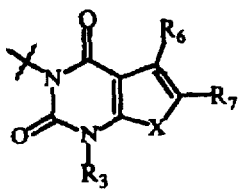 --

Signed and Sealed this

Thirtieth Day of April, 2002

Attest:

JAMES E. ROGAN  
*Attesting Officer*    *Director of the United States Patent and Trademark Office*